(12) United States Patent
Urano et al.

(10) Patent No.: US 12,055,546 B2
(45) Date of Patent: Aug. 6, 2024

(54) FLUORESCENT PROBE FOR DETECTING CARBOXYPEPTIDASE ACTIVITY

(71) Applicant: THE UNIVERSITY OF TOKYO, Tokyo (JP)

(72) Inventors: Yasuteru Urano, Tokyo (JP); Mako Kamiya, Tokyo (JP); Minoru Kawatani, Tokyo (JP); Hirohisa Iwaki, Tokyo (JP); Kyoko Yamamoto, Tokyo (JP); Haruki Kume, Tokyo (JP); Daisuke Yamada, Tokyo (JP)

(73) Assignee: The University of Tokyo, Tokyo (JP)

( * ) Notice: Subject to any disclaimer, the term of this patent is extended or adjusted under 35 U.S.C. 154(b) by 1009 days.

(21) Appl. No.: 16/977,434

(22) PCT Filed: Mar. 4, 2019

(86) PCT No.: PCT/JP2019/008403
§ 371 (c)(1),
(2) Date: Nov. 13, 2020

(87) PCT Pub. No.: WO2019/168199
PCT Pub. Date: Sep. 6, 2019

(65) Prior Publication Data
US 2021/0072241 A1 Mar. 11, 2021

(30) Foreign Application Priority Data
Mar. 2, 2018 (JP) .................................. 2018-037791

(51) Int. Cl.
*C07D 311/90* (2006.01)
*C07D 493/10* (2006.01)
*G01N 33/573* (2006.01)
*G01N 33/574* (2006.01)

(52) U.S. Cl.
CPC ......... *G01N 33/573* (2013.01); *C07D 311/90* (2013.01); *C07D 493/10* (2013.01); *G01N 33/57434* (2013.01)

(58) Field of Classification Search
None
See application file for complete search history.

(56) References Cited

U.S. PATENT DOCUMENTS

2006/0003383 A1 1/2006 Graham
2009/0047699 A1 2/2009 Graham

OTHER PUBLICATIONS

Appelros et al., Activation Peptide of Carboxypeptidase B in Serum and Urine in Acute Pancreatitis, Gut, vol. 42, pp. 97-102, 1998.
Hooper, Angiotensin Converting Enzyme: Implications from Molecular Biology for its Physiological Functions, International Journal of Biochemistry, vol. 23, pp. 641-647, 1991.
Kawatani et al., Development of a Novel Activatable Fluorescence Probe for Detection of Carboxypeptidase Activity Based on Azoformyl Group, Presentation Abstracts of the 138th Annual Meeting (Kanazawa) of the Pharmaceutical Society of Japan, 26V-pm11S, http://nenkai.pharm.or.jp/138/pc/isearch/asp, Feb. 1, 2018 [Retrieved May 22, 2019].
Kido et al., CPM is a Useful Cell Surface Marker to Isolate Expandable Bi-Potential Liver Progenitor Cells Derived from Human IPS Cells, Stem Cell Reports, vol. 5, pp. 508-515, 2015.
Kuriki et al., Establishment of Molecular Design Strategy to Obtain Activatable Fluorescent Probes for Carboxypeptidases, Journal of the American Chemical Society, vol. 140, No. 5, pp. 1767-1773, 2018.
Mock et al., Arazoformyl Peptide Surrogates as Spectrophotometric Kinetic Asay Substrates for Carboxypeptidase A, Analytical Biochemistry, vol. 239, No. 2, pp. 218-222, 1996.
Mock et al., Catalytic Activity of Carboxypeptidase B and of Carboxypeptidase Y with Anisylazoformyl Substrates, Bioorganic & Medicinal Chemistry Letters, vol. 9, No. 2, pp. 187-192, 1999.
Rawlings et al., Handbook of Proteolytic Enzymes, 3rd Edition, Elsevier, 2013.
Silver et al., Prostate-Specific Membrane Antigen Expression in Normal and Malignant Human Tissues, Clinical Cancer Research, vol. 3 , pp. 81-85, 1997.
International Search Report, dated Jun. 4, 2019, in International Application No. PCT/JP2019/008403.
Written Opinion, dated Jun. 4, 2019, in International Application No. PCT/JP2019/008403.

*Primary Examiner* — Samantha L Shterengarts
(74) *Attorney, Agent, or Firm* — Knobbe, Martens, Olson & Bear, LLP

(57) ABSTRACT

A fluorescent probe can be used to detect and visualize carboxypeptidase activity with high sensitivity. The fluorescent probe has, as a base nucleus, a fluorescent skeleton that functions in the visible light region, and makes carboxypeptidase activity detectable and visible, for example, within a cell or clinical specimen, with high sensitivity.

14 Claims, 20 Drawing Sheets

[Fig. 1]
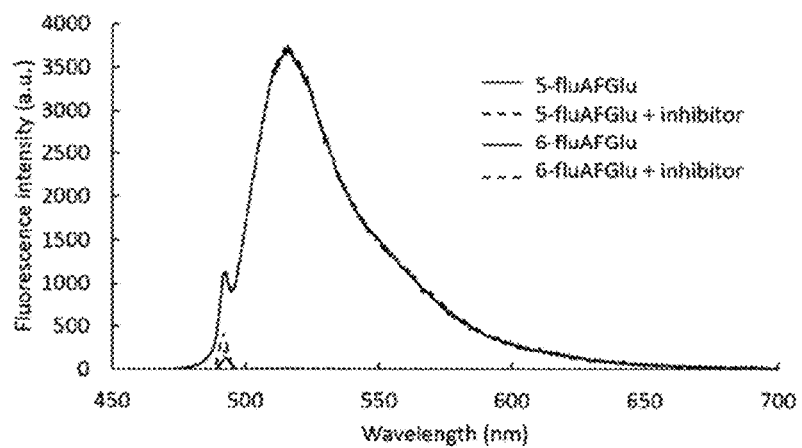
[Fig. 2]
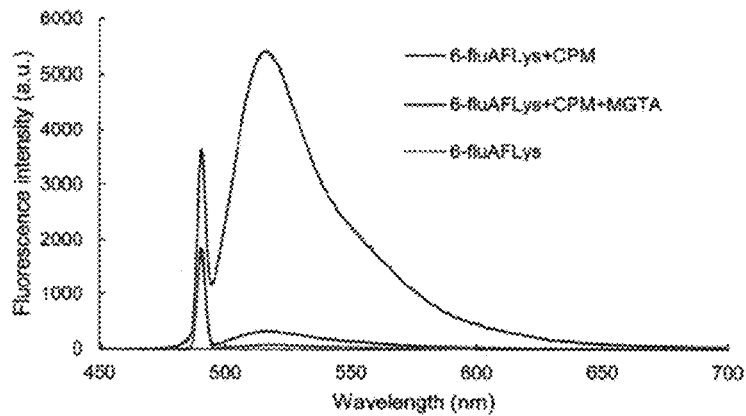

[Fig. 3]
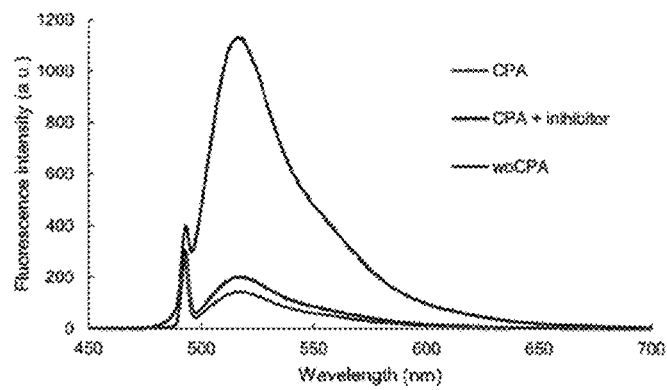
[Fig. 4]
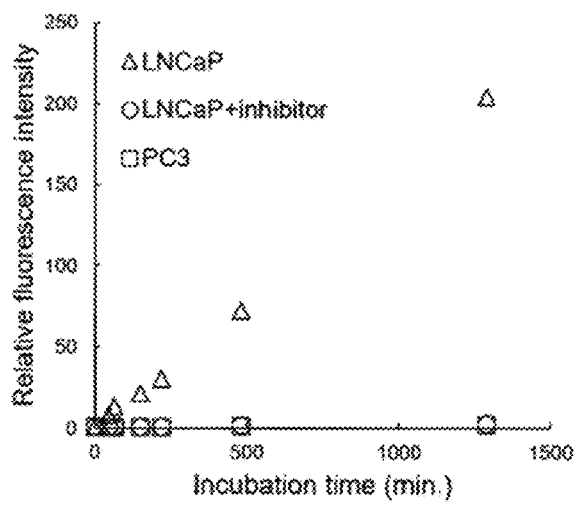

[Fig. 5]
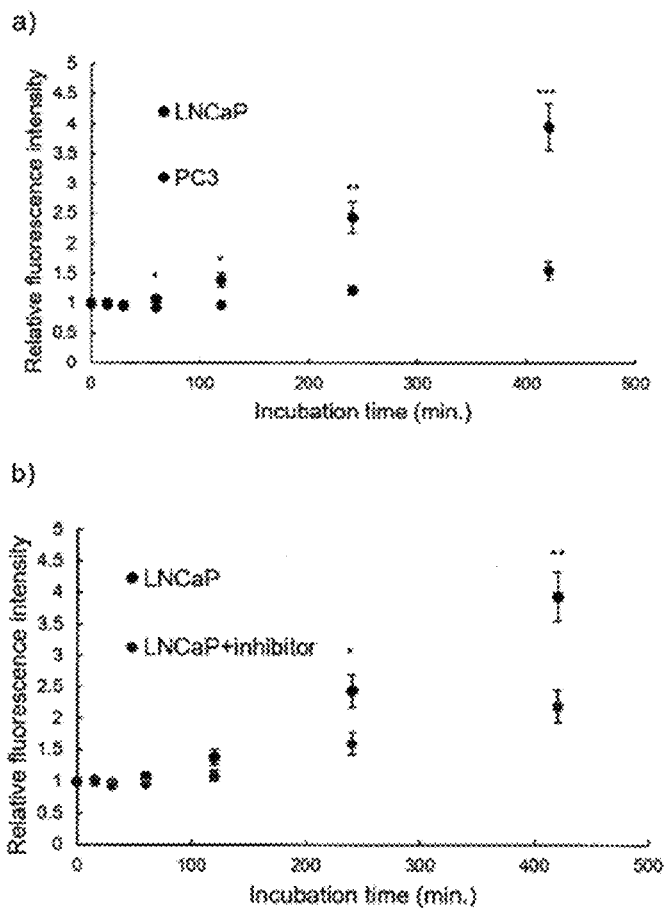
[Fig. 6]
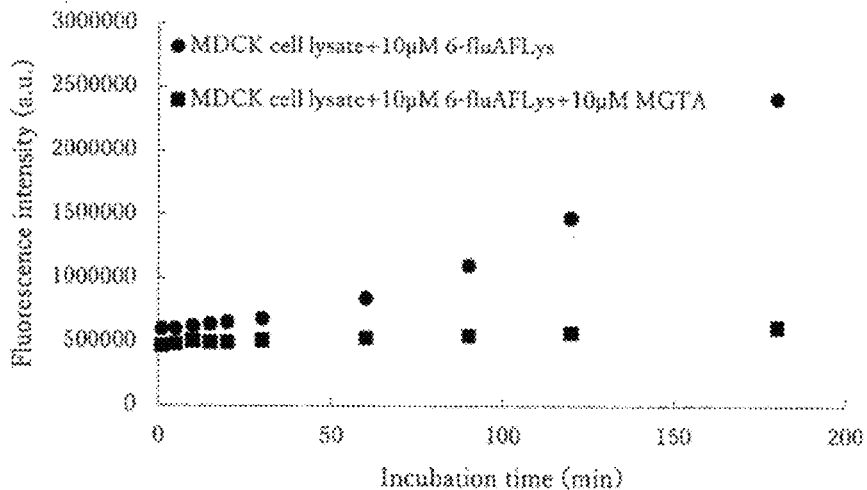

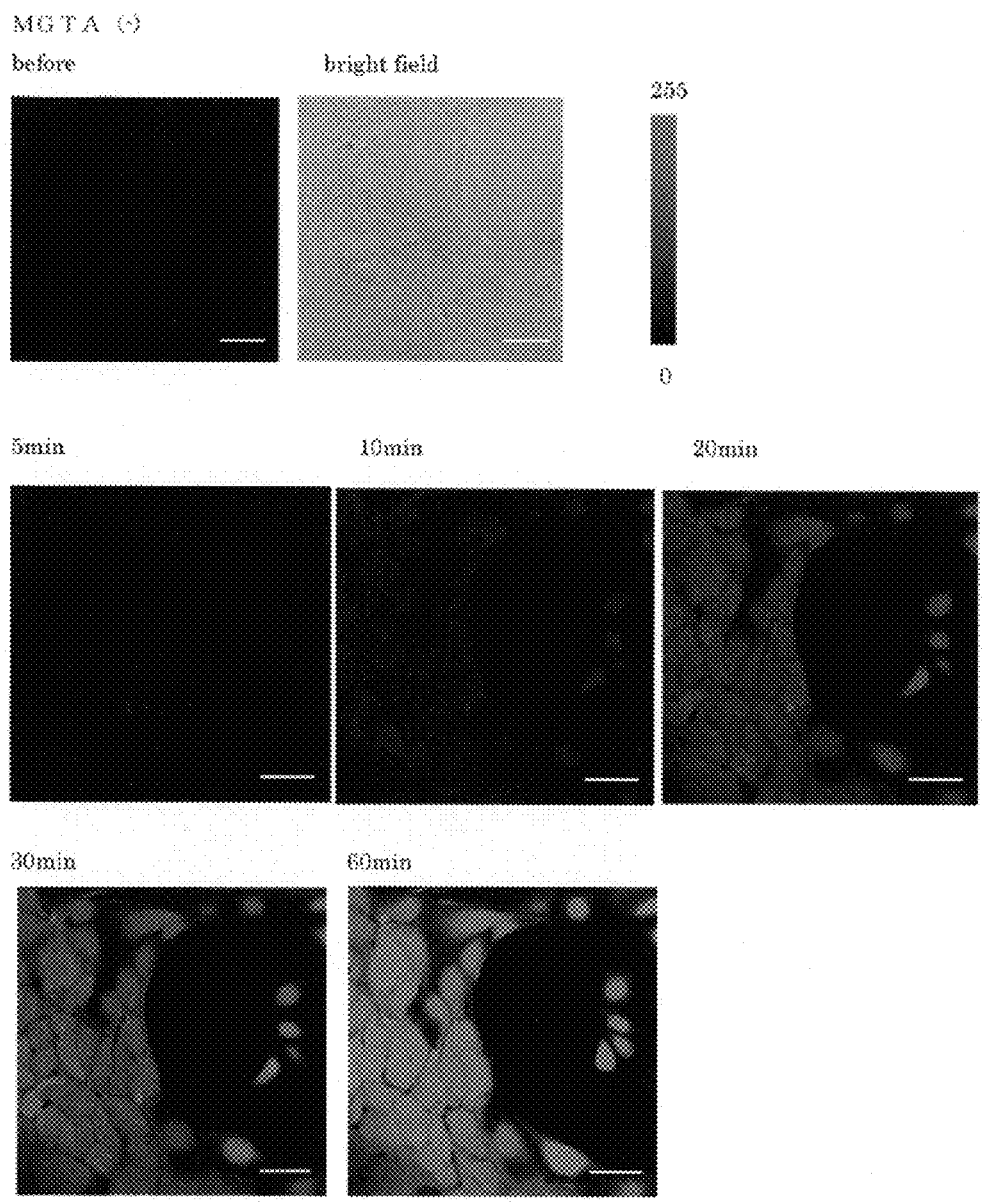
[Fig. 7]

[Fig. 8]
MGTA (+)
Before
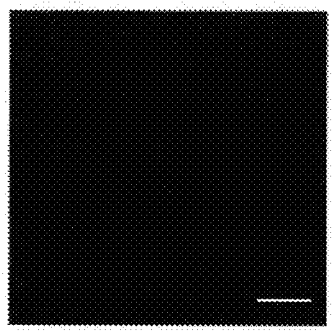
bright field
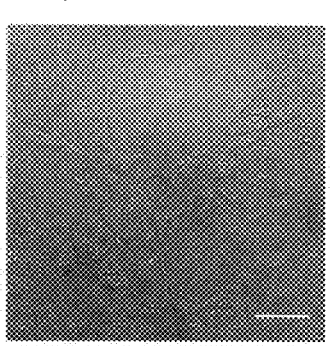
5min
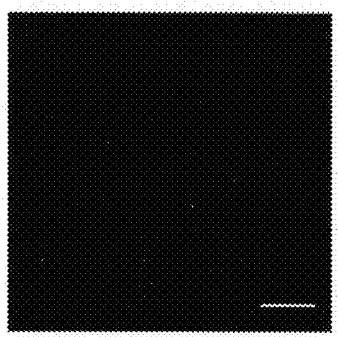
10min
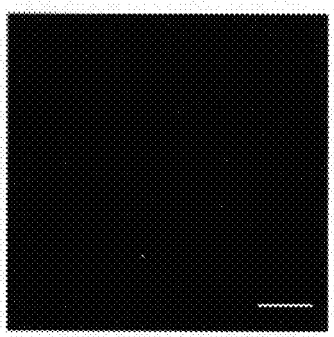
20min
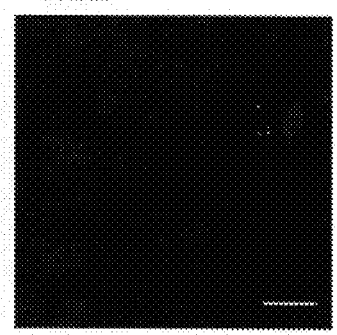
30min
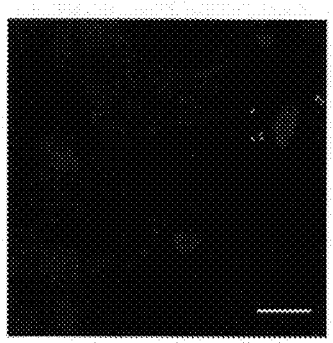
60min
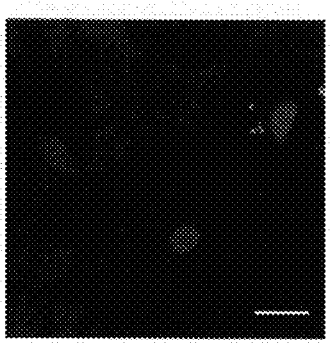

[Fig. 9]
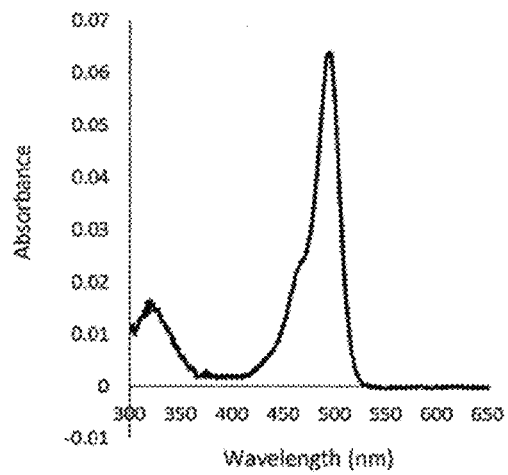
[Fig. 10]
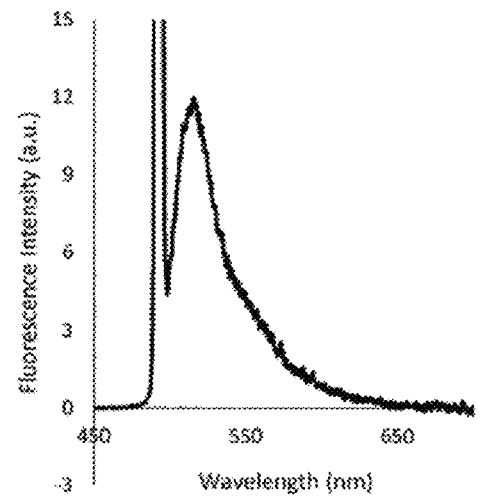

[Fig. 11]
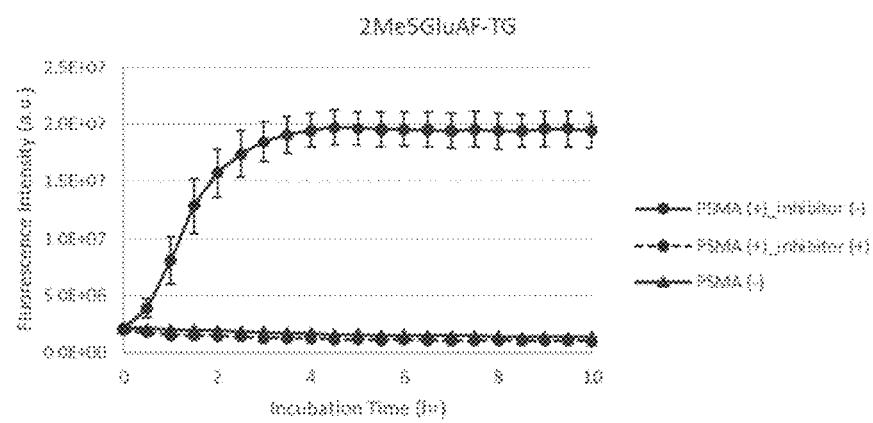
[Fig. 12]
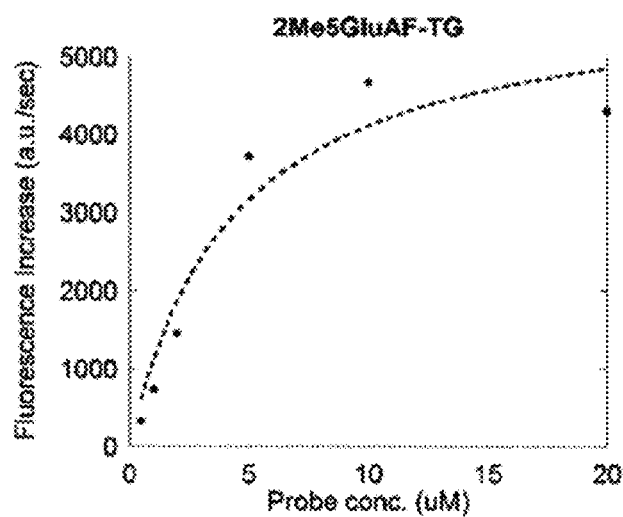

[Fig. 13]
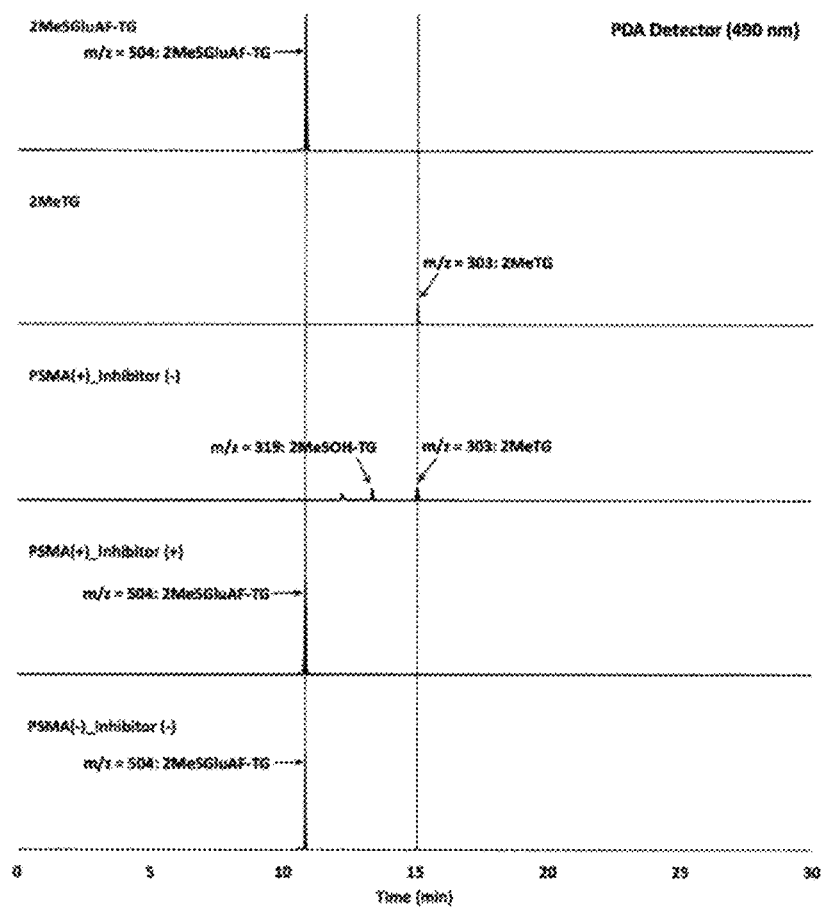

[Fig. 14]
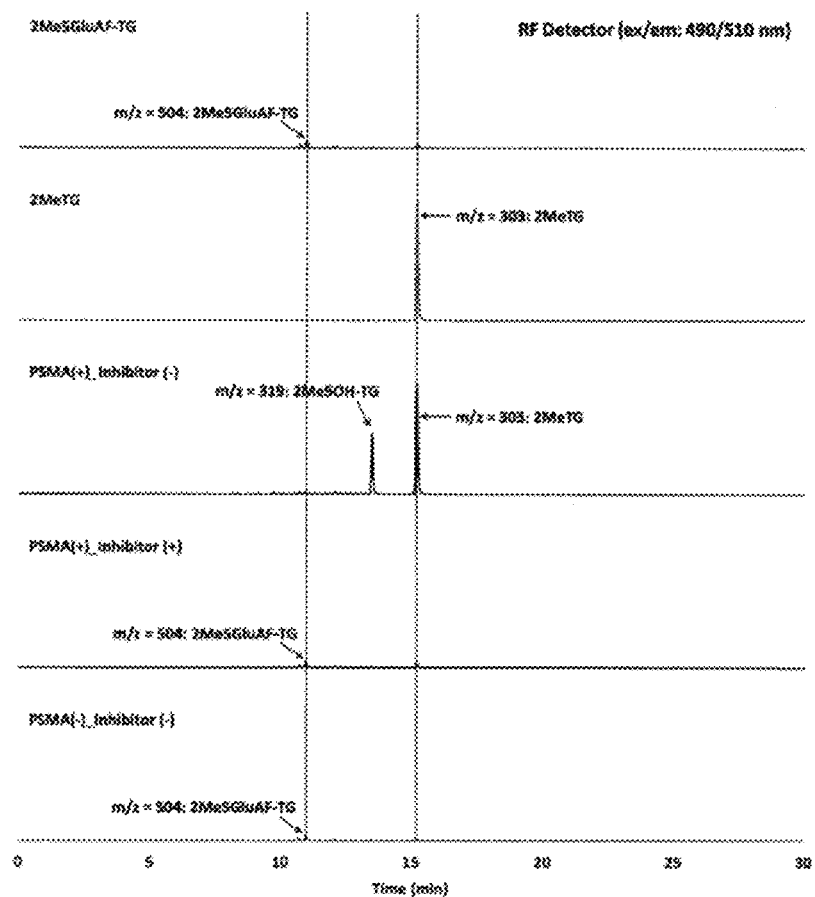

[Fig. 15]
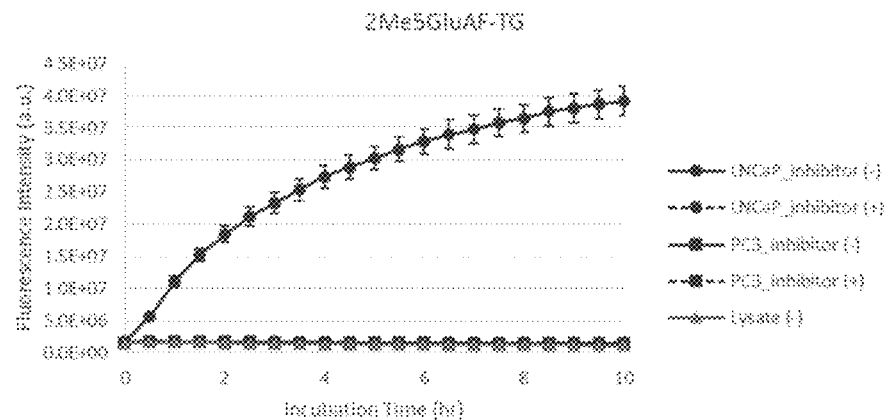
[Fig. 16]
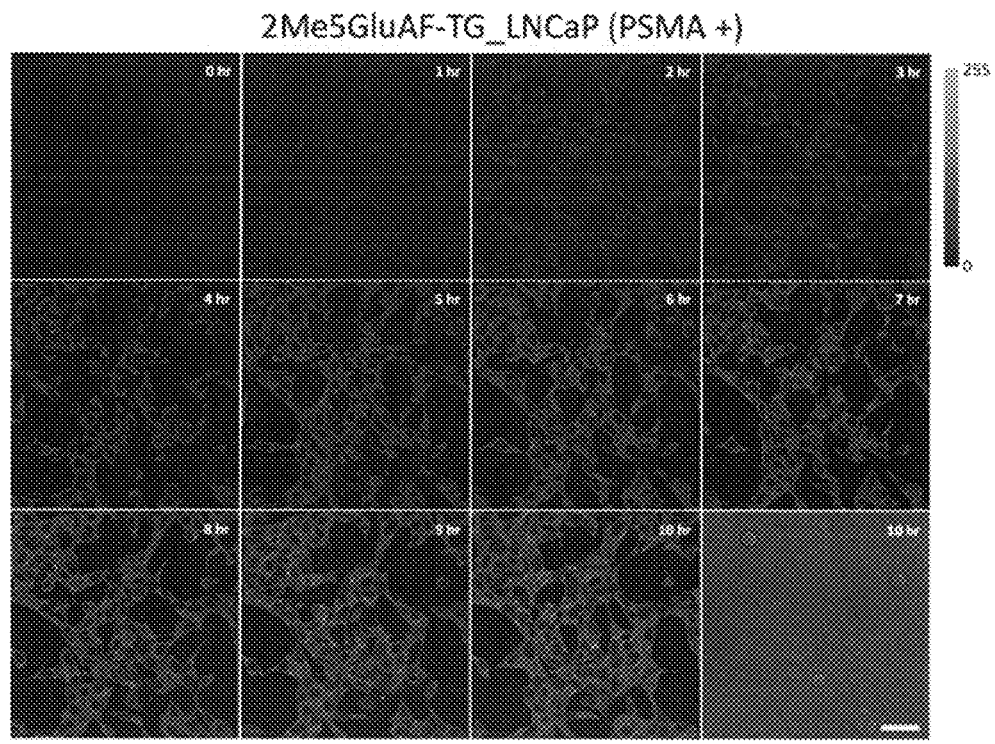

[Fig. 17]
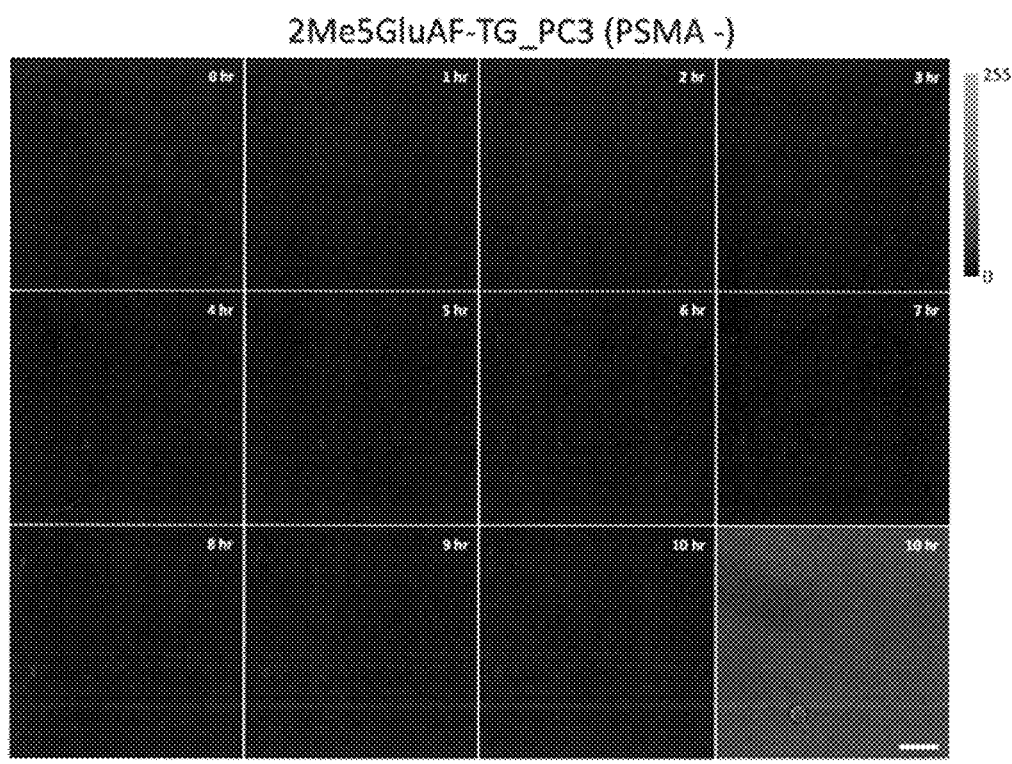

[Fig. 18a]
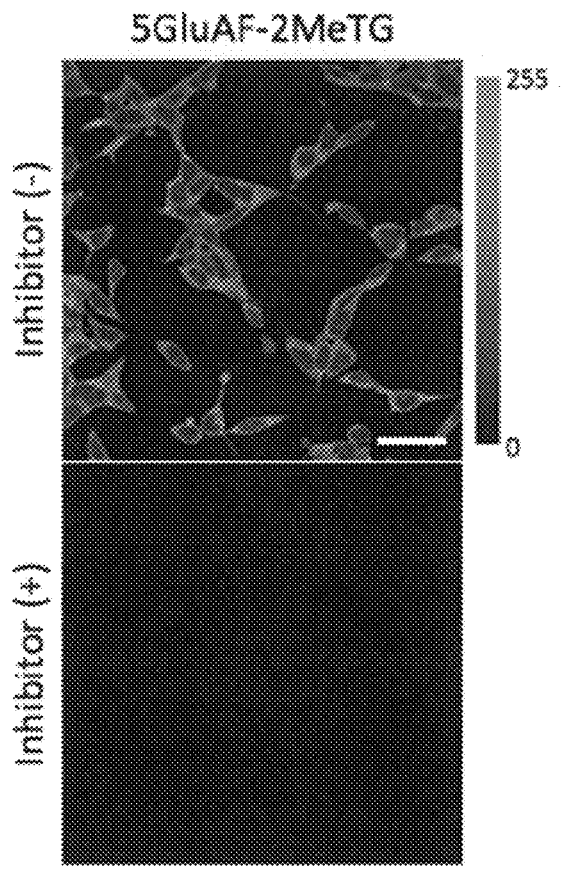
[Fig. 18b]
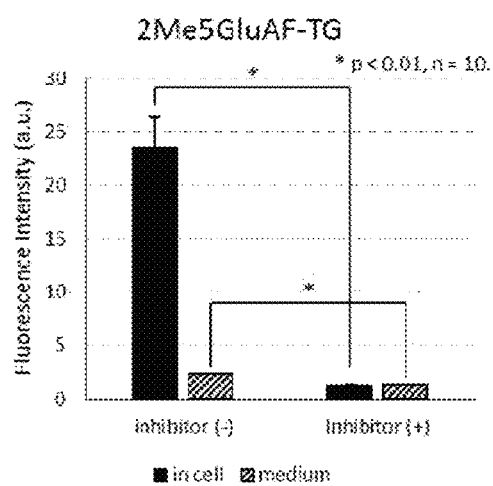

[Fig. 19]
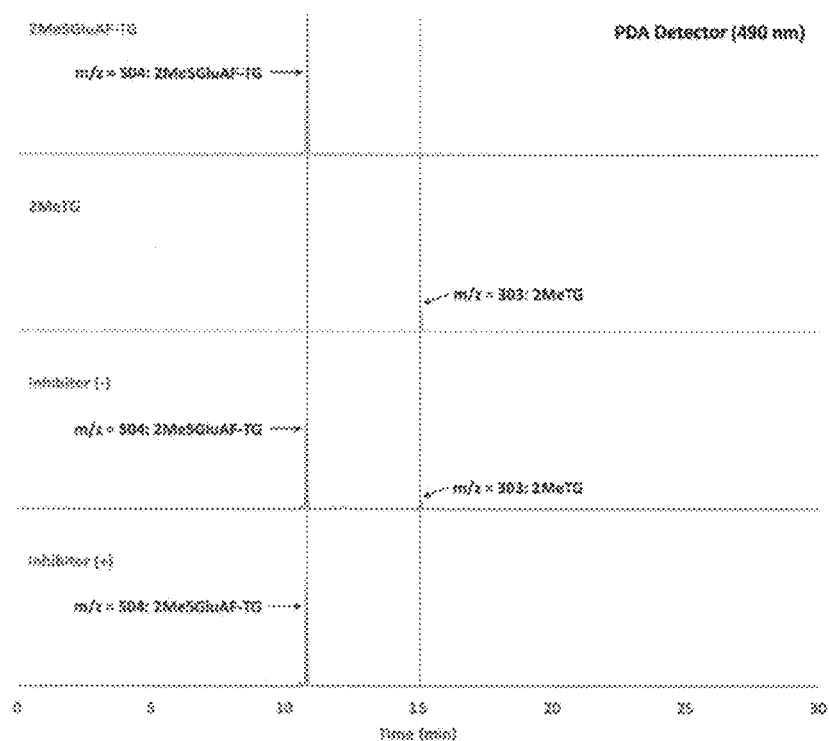

[Fig. 20]
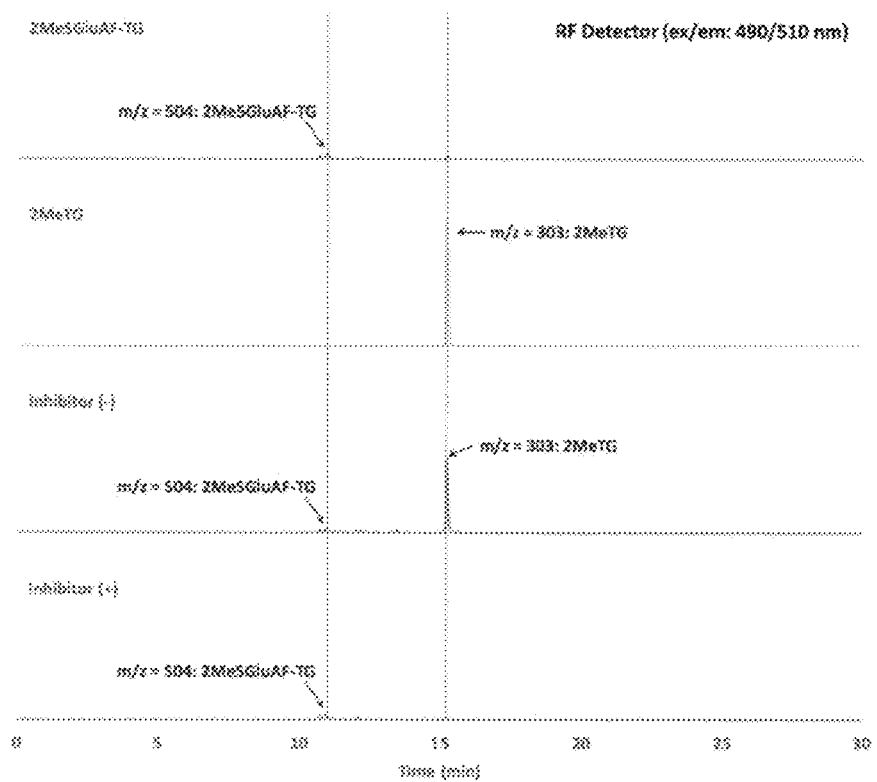

[Fig. 21]
(a)
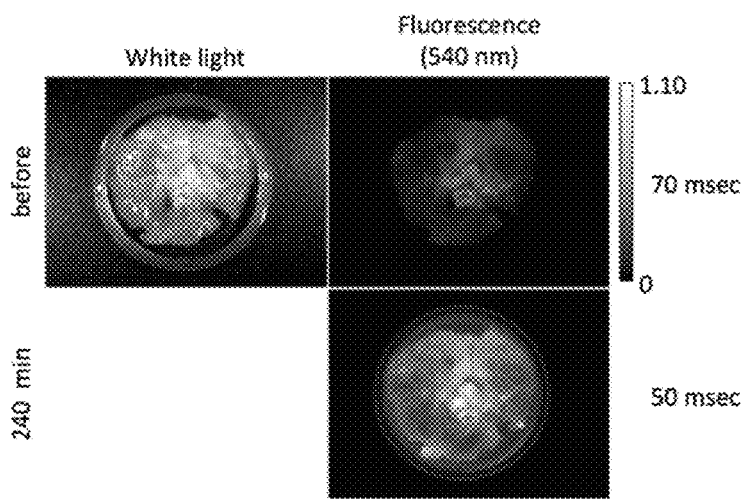
(b)
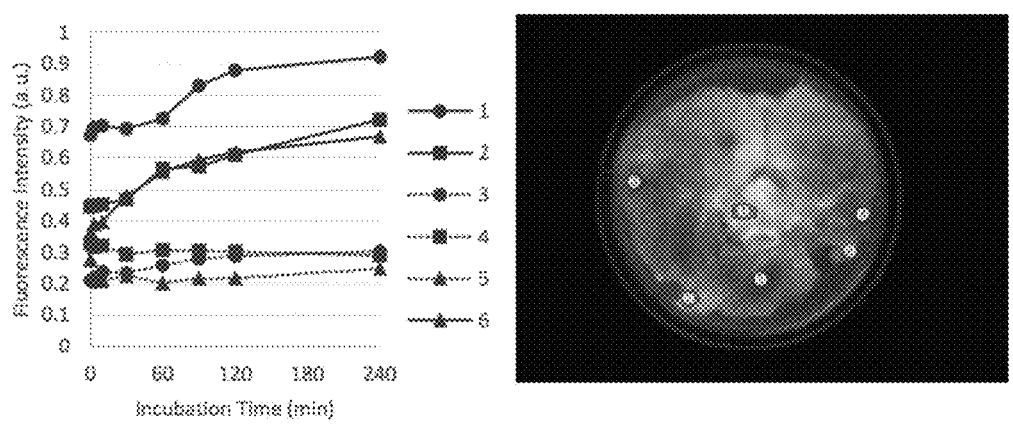
(c)
| | Activation ratio | | PSMA EXPRESSION | CANCER RATE | GS |
|---|---|---|---|---|---|
| | 30min-0min | 60min-0min | | | |
| 1-1 | 0.02 | 0.052 | 3 | 0 | - |
| 1-2 | 0.024 | 0.121 | 4 | 40 | 4+4 |
| 1-3 | 0.025 | 0.049 | 2 | 0 | - |
| 1-4 | -0.035 | -0.02 | 1 | 0 | - |
| 1-5 | -0.06 | -0.073 | 4 | 0 | - |
| 1-6 | 0.113 | 0.192 | 3 | 15 | 3+3 |

[Fig. 22]
(a)
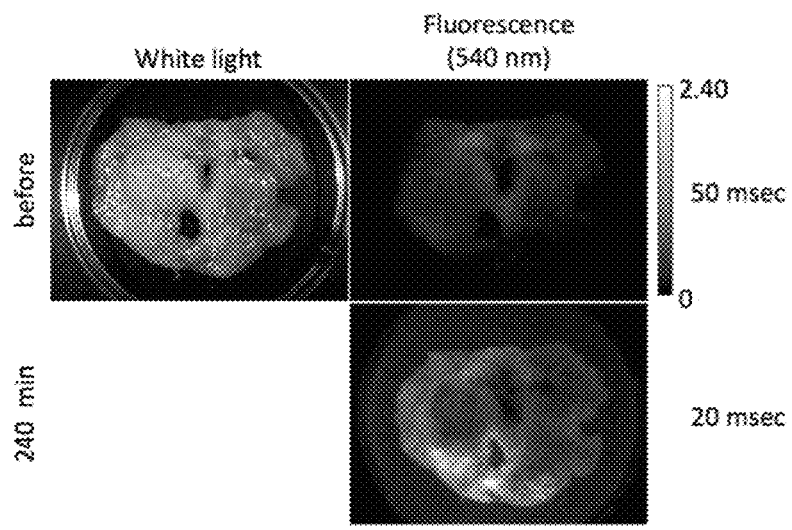
(b)
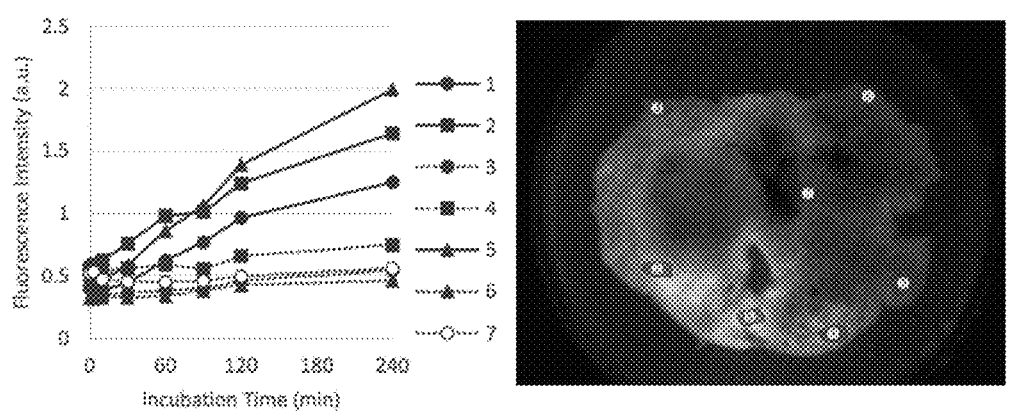
(c)
| | Activation ratio | | PSMA EXPRESSION | CANCER RATE | GS |
|---|---|---|---|---|---|
| | 30min-0min | 60min-0min | | | |
| 2-1 | 0.048 | 0.225 | 4 | 85 | 3+4 |
| 2-2 | 0.194 | 0.417 | 3 | 80 | 3+4 |
| 2-3 | -0.045 | -0.02 | 1 | 45 | 3+3 |
| 2-4 | 0.023 | 0.055 | 2 | 0 | (WITH PIN) |
| 2-5 | 0.084 | 0.357 | 3 | 85 | 3+4 |
| 2-6 | 0.003 | 0.012 | 1 | 0 | - |
| 2-7 | -0.066 | -0.068 | 2 | 0 | - |

[Fig. 23]
(a)
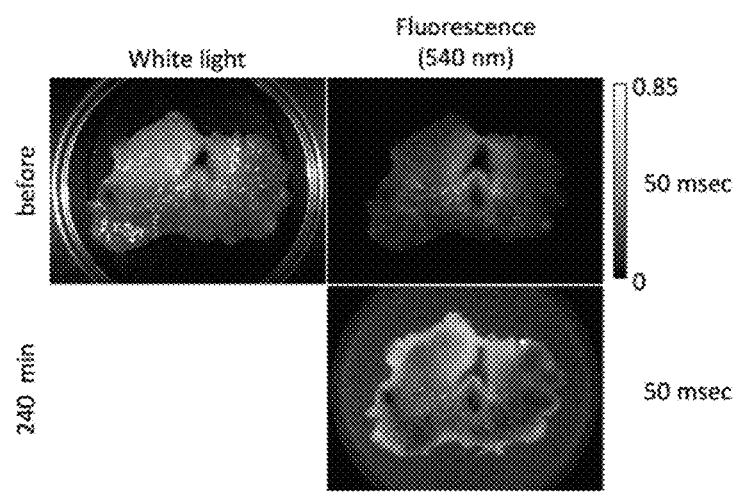
(b)
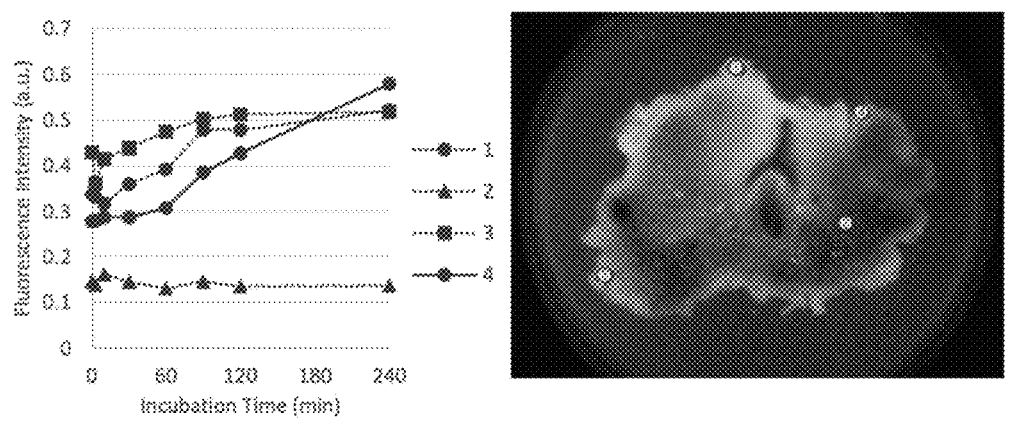
(c)
| | Activation ratio | | PSMA EXPRESSION | CANCER RATE | GS |
|---|---|---|---|---|---|
| | 30min-0min | 60min-0min | | | |
| 3-1 | 0.022 | 0.055 | 1 | 0 | - |
| 3-2 | -0.001 | -0.016 | 2*2 | 5 | 3+4 |
| 3-3 | 0.009 | 0.046 | 2 | 5 | 3+3 |
| 3-4 | 0.008 | 0.029 | 2*2 | 15 | 3+3 |
*1: PSMA STAINS INTENSELY WITH CANCER
*2: PSMA DOES NOT STAIN WITH CANCER

[Fig. 24]
(a)
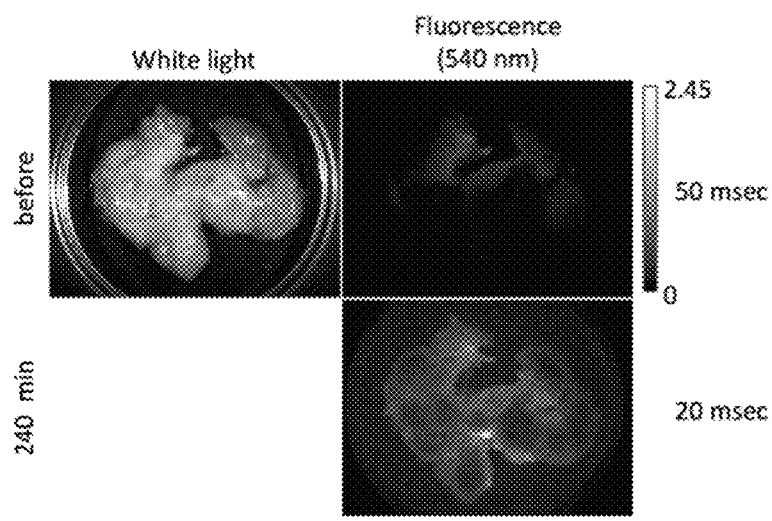
(b)
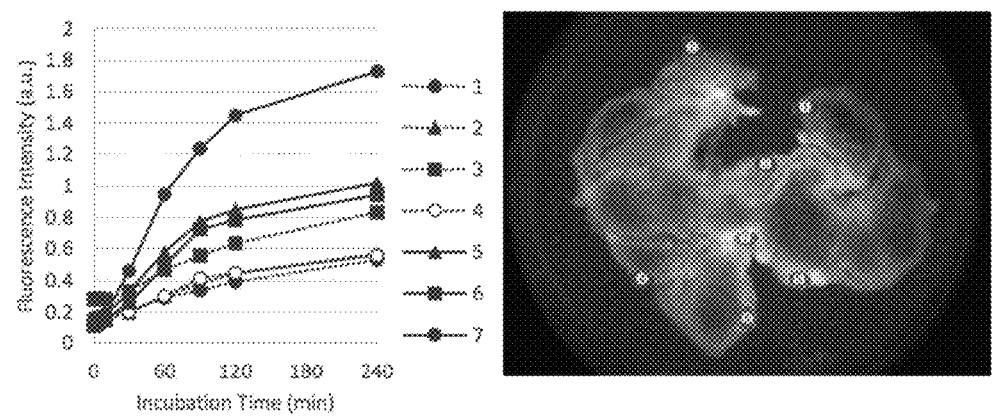
(c)
| | Activation ratio | | PSMA EXPRESSION | CANCER RATE | GS |
|---|---|---|---|---|---|
| | 30min-0min | 60min-0min | | | |
| 4-1 | 0.044 | 0.123 | 2 | 0 | - |
| 4-2 | 0.046 | 0.151 | 1 | 0 | - |
| 4-3 | 0.051 | 0.186 | 1 | 0 | - |
| 4-4 | 0.077 | 0.182 | 3 | 60 | 4+3 |
| 4-5 | 0.191 | 0.443 | 3 | 60 | 4+3 |
| 4-6 | 0.146 | 0.383 | 4 | 80 | 4+3 |
| 4-7 | 0.325 | 0.815 | 4 | 95 | 3+4 |

[Fig. 25]
(a)
CHANGE METHOD SO THAT SURFACE IS COVERED WITH GAUZE SOAKED IN PROBE SOLUTION. TEMPORARILY REMOVE GAUZE, AND TAKE FLUORESCENCE IMAGE
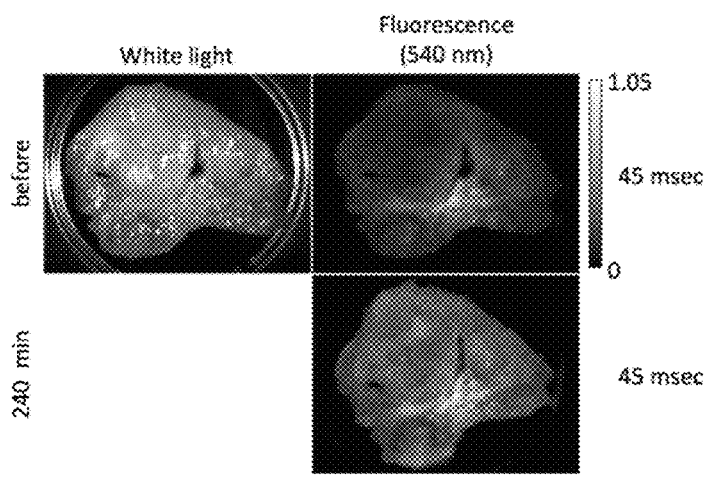
(b)
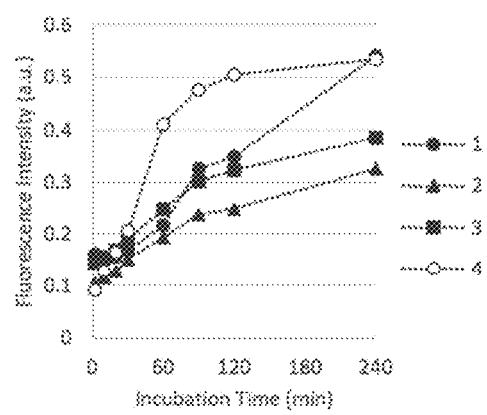 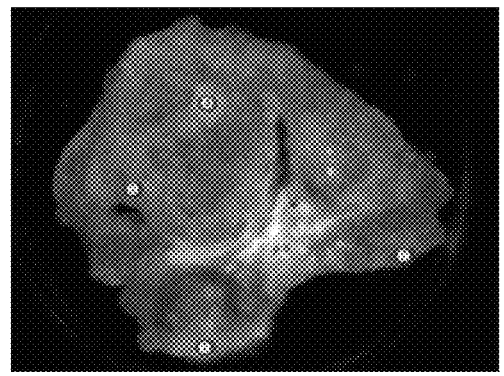
(c)
| | Activation ratio | | | | |
| --- | --- | --- | --- | --- | --- |
| | 30min-0min | 60min-0min | PSMA EXPRESSION | CANCER RATE | GS |
| 5-1 | 0.006 | 0.055 | 2 | 0 | - |
| 5-2 | 0.047 | 0.089 | 2 | 15 | 3+4 |
| 5-3 | 0.044 | 0.103 | 3 | 90 | 3+4 |
| 5-4 | 0.1157 | 0.3187 | 4 | 85 | 4+3 |

[Fig. 26]
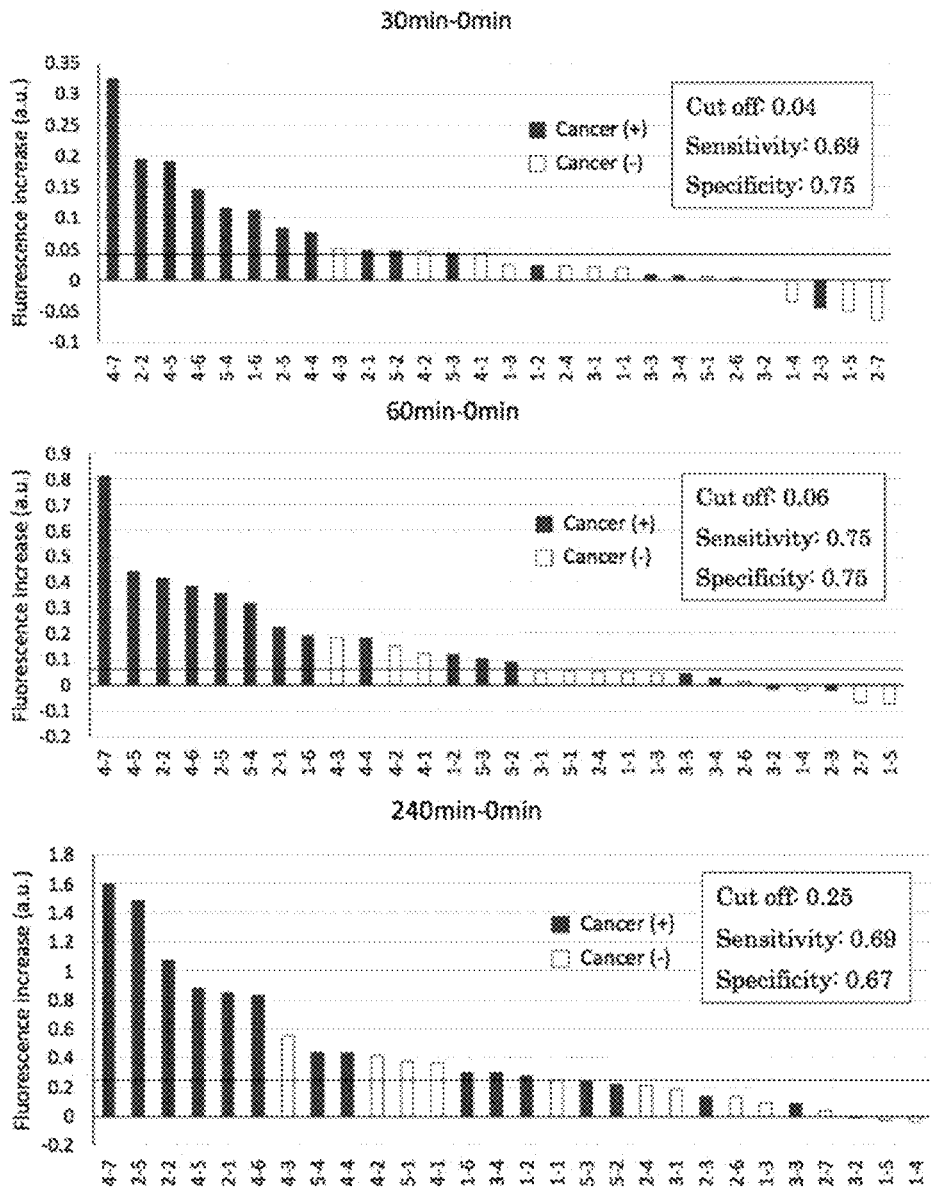

FLUORESCENT PROBE FOR DETECTING CARBOXYPEPTIDASE ACTIVITY

PRIORITY AND CROSS REFERENCE TO RELATED APPLICATIONS

This application is the U.S. National Phase Application under 35 U.S.C. § 371 of International Application No. PCT/JP2019/008403, filed Mar. 4, 2019, designating the U.S. and published as WO 2019/168199 A1 on Sep. 6, 2019, which claims the benefit of Japanese Application No. JP 2018-037791, filed Mar. 2, 2018. Any and all applications for which a foreign or a domestic priority is claimed is/are identified in the Application Data Sheet filed herewith and is/are hereby incorporated by reference in their entirety.

TECHNICAL FIELD

The present invention relates to a novel fluorescent probe for detecting carboxypeptidase activity.

BACKGROUND ART

A cancer is a disease that accounts for about 30% of causes of deaths of Japanese, and surgical extirpation of the cancer is one of the most effective therapeutic methods under the present circumstances. However, it is difficult to find a cancer having an invisible size and reliably remove the cancer, which causes recurrence. Thus, in order to visualize a minute cancer, the research group of the present inventors has developed a fluorescent probe for detecting activity of an aminopeptidase highly expressed in a cancer-specific manner. However, on the other hand, a portion of carboxypeptidase which is carboxy-terminal hydrolase of protein is also known as a cancer marker.

Carboxypeptidase is a generic term for a group of enzymes that recognizes a C-terminal amino acid of a peptide chain and is cleaved by hydrolysis, and relations with various life phenomena and diseases have been reported so far (Non-Patent Literature 1). For example, it has been reported that prostate specific membrane antigen (PSMA) is a clinically important target enzyme group as a biomarker for prostate cancer (Non-Patent Literature 2), and carboxypeptidase B is a clinically important target enzyme group as a biomarker for pancreatic disease (Non-Patent Literature 3).

In addition, carboxypepitdase M has been reported as a marker for differentiation from iPS cells to hepatic progenitor cells (Non-Patent Literature 4). Moreover, inhibitors of angiotensin converting enzyme (ACE) are widely used as antihypertensive drugs and are important as drug targets (Non-Patent Literature 5). As described above, carboxypeptidase is an important enzyme group from the viewpoint of drug discovery and diagnosis as well as biological research.

Due to the importance as described above, many methods for detecting enzymatic activity of carboxypeptidase have been developed so far. However, most of the methods require complicated operations such as fluorescent derivatization and extraction of an enzyme reaction product and use of a radioactive isotope, etc., which pose a problem in measurement simplicity and the like.

Although a fluorescent substrate has been reported, which is of a type in which some carboxypeptidases are used as targets and the fluorescence is increased by metabolism of a substrate with an enzyme, since an enzyme recognition site is used for fluorescence control, not only the type of the substrate is extremely limited, but excitation by ultraviolet light is required, and therefore, the fluorescent substrate has a problem difficult to be applied to living cells or in vivo.

A conventional fluorescent probe for detecting carboxypeptidase activity has two reaction points, and there is a problem that detection requires time. There is also a problem that PSMA which is a clinically important cancer marker does not recognize the substrate and the carboxypeptidase activity cannot be detected.

CITATION LIST

Non-Patent Literature

Non-Patent Literature 1: Rawlings, N. D. & Salvesen, G. Handbook of Proteolytic Enzymes 3rd Edition. elsevier (2013).

Non-Patent Literature 2: Silver, D. A., Pellicer, I., Fair, W. R., Heston, W. D. W. & Cordon-Cardo, C. Prostate-specific membrane antigen expression in normal and malignant human tissues. Clin. cancer Res. 3, 81-85 (1997).

Non-Patent Literature 3: Appelros, S., Thim, L. & Borgstrom, a. Activation peptide of carboxypeptidase B in serum and urine in acute pancreatitis. Gut 42, 97-102 (1998).

Non-Patent Literature 4: Kido, T., Koui, Y., Suzuki, K., Kobayashi, A., Miura, Y., Chern, E. Y., Tanaka, M. & Miyajima, A. CPM is a useful cell surface marker to isolate expandable bi-potential liver progenitor cells derived from human iPS cells. Stem Cell Reports 5, 508-515 (2015).

Non-Patent Literature 5: Hooper, N. M. Angiotensin converting enzyme: Implications from molecular biology for its physiological functions. Int. J. Biochem. 23, 641-647 (1991).

Non-Patent Literature 6: Kuriki, Y., Kamiya, M., Kubo, H., Komatsu, T., Ueno, T., Tachibana, R., Hayashi, K., Hanaoka, K., Yamashita, S., Ishizawa, T., Kokudo, N. & Urano, Y. Establishment of molecular design strategy to obtain activatable fluorescent probes for carboxypeptidases. submitted

SUMMARY

It is an object of the present invention to provide a fluorescent probe that can visualize carboxypeptidase activity with high sensitivity by using a fluorescent skeleton that functions in a visible light region as a mother nucleus.

The present inventors have conducted extensive studies to solve the above problems, and as a result, an azoamide group showing a spontaneous decarboxylation/denitrification reaction with hydrolysis of a substrate amino acid is introduced with respect to a skeleton of a fluorescent dye such as fluorescein, so that the inventors have succeeded in establishing a fluorescent probe design method applicable to any general carboxypeptidase activity capable of being detected with high sensitivity while suppressing the number of reaction points to one, and have completed the present invention.

In other words, the present invention provides:

[1] a compound represented by the following general formula (I) or a salt thereof.

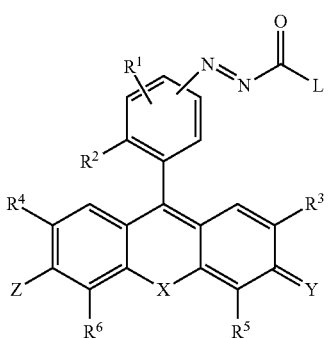

(where:
R$^1$ represents a hydrogen atom or one to three monovalent substituent groups present on a benzene ring, which are the same or different;

R$^2$ represents a monovalent substituent group present on a benzene ring;

R$^3$ and R$^4$ are, each independently, a hydrogen atom, an alkyl group having 1 to 6 carbon atoms, or a halogen atom;

R$^5$ and R$^6$ are, each independently, a hydrogen atom, an alkyl group having 1 to 6 carbon atoms, or a halogen atom;

L represents an amino acid residue;

X is selected from an oxygen atom, Si(R$^a$) (R$^b$), C (R$^a$) (R$^b$), Ge(R$^a$) (R$^b$), P(=O) R$^c$ or Se where:

R$^a$ and R$^b$ are, each independently, an alkyl group having 1 to 6 carbon atoms or an aryl group optionally being substituted, and R$^c$ is an alkyl group having 1 to 6 carbon atoms or a phenyl group optionally being substituted;

Y and Z are selected from a pair of (0, OH), (NR$^7$R$^8$, NR$^9$R$^{10}$), and (O, NR$^9$R$^{10}$)

where:

R$^7$ and R$^8$ are, each independently, a hydrogen atom or an alkyl group having 1 to 3 carbon atoms;

R$^7$ and R$^8$ together optionally form a 4-7 membered heterocyclyl containing a nitrogen atom to which R$^7$ and R$^8$ are bonded;

R$^7$ or R$^8$, or both R$^7$ and R$^8$, together with R$^3$ and/or R$^5$, respectively, optionally form a 5-7 membered heterocyclyl or heteroaryl containing a nitrogen atom to which R$^7$ and/or R$^8$ are bonded, and optionally contain from one to three heteroatoms selected from the group consisting of an oxygen atom, nitrogen atom, and sulfur atom as ring-constituting members, and the heterocyclyl or heteroaryl is optionally substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms;

R$^9$ and R$^{10}$ are, each independently, a hydrogen atom or an alkyl group having 1 to 3 carbon atoms;

R$^9$ and R$^{10}$ together optionally form a 4-7 membered heterocyclyl containing a nitrogen atom to which R$^9$ and R$^{10}$ are bonded;

R$^9$ or R$^{10}$, or both R$^9$ and R$^{10}$, together with R$^4$ and/or R$^6$, respectively, optionally form a 5-7 membered heterocyclyl or heteroaryl containing a nitrogen atom to which R$^9$ and/or R$^{10}$ are bonded, and optionally contain from one to three heteroatoms selected from the group consisting of an oxygen atom, nitrogen atom, and sulfur atom as ring-constituting members, and the heterocyclyl or heteroaryl is optionally substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms; and when Y and Z are 0 and OH, respectively, and when a monovalent substituent group present on a benzene ring of R$^2$ is a carboxyl group, Y and Z are optionally acetylated.)

[2] The compound or salt thereof according to [1], wherein L is represented by the following formula.

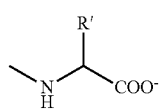

(where R' represents a side chain of an amino acid.)

[3] The compound or salt thereof according to [1] or [2], wherein the monovalent substituent of R$^2$ is selected from an alkyl group having 1 to 6 carbon atoms, a hydroxyalkyl group having 1 to 6 carbon atoms, an alkoxy group having 1 to 6 carbon atoms, an aminoalkyl group having 1 to 6 carbon atoms, a carboxyl group, an alkoxycarbonyl group, an amide group or a carboxamide group optionally having a substituent on nitrogen.

[4] The compound or salt thereof according to any one of [1] to [3], wherein X is an oxygen atom.

[5] The compound or salt thereof according to any one of [1] to [4], wherein Y and Z are 0 and OH, respectively, the monovalent substituent group present on the benzene ring of R$^2$ is a carboxyl group, Y and Z are acetylated, and represented by the following general formula (V).

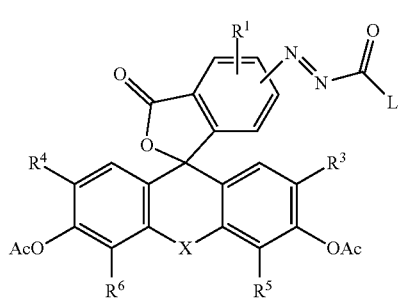

(where Ac represents an acetyl group.)

[6] A compound selected from the following formulas, or a salt thereof.

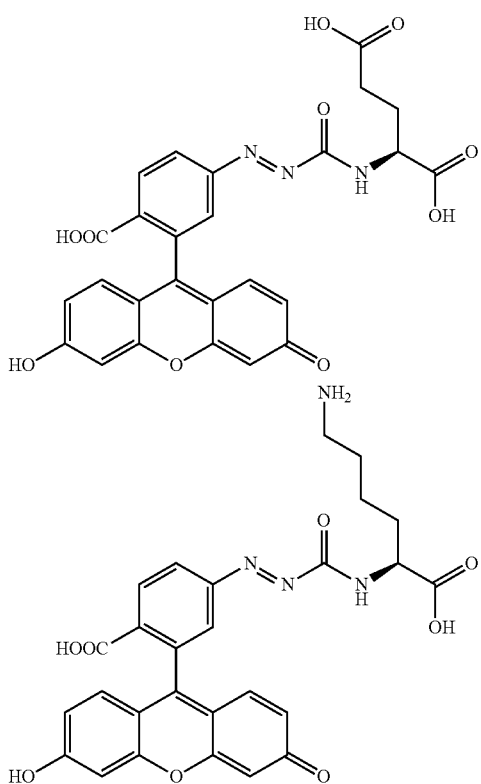

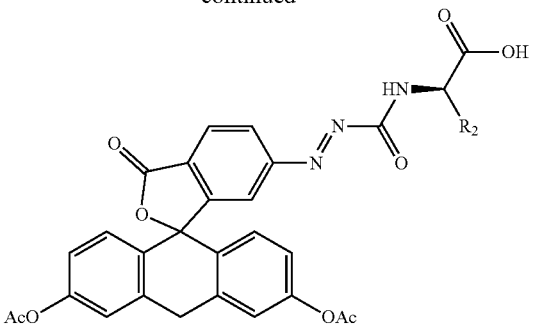

(R₂ is $CH_2CH_2COOH$ or $CH_2CH_2CH_2CH_2NH_2$)

[7] A fluorescent probe for detecting carboxypeptidase activity comprising the compound or salt thereof according to any one of [1] to [6].

[8] A method of detecting carboxypeptidase in a cell, comprising:
(a) introducing the fluorescent probe according to [7] into the cell; and,
(b) measuring fluorescence emitted in the cell by the fluorescent probe.

[9] A method of detecting a prostate cancer, comprising:
(a) applying the fluorescent probe according to [7] to a clinical specimen of prostate; and,
(b) measuring a fluorescence image of a surgical specimen of the prostate to which the fluorescent probe is applied.

The fluorescent probe according to the present invention has an amino acid recognized by target carboxypeptidase and is almost non-fluorescent before a reaction with the target carboxypeptidase. However, since a reaction with an enzyme may restore the fluorescence in a visible light region, the carboxypeptidase activity can be visualized with high sensitivity.

When the fluorescent probe of the present invention is applied to an in vitro enzyme system or a cultured cell system, the target carboxypeptidase activity can be rapidly subjected to fluorescence detection.

By applying the fluorescent probe of the present invention, it is considered that a cancer in a clinical specimen can be visualized, and the fluorescent probe is particularly effective in visualizing prostate cancer.

BRIEF DESCRIPTION OF DRAWINGS

FIG. 1 illustrates a fluorescence spectrum of 5-fluAFGlu and 6-fluAFGlu after addition of PSMA and an inhibitor (2-PMPA, 10 μM).

FIG. 2 illustrates a fluorescence spectrum of 6-fluAFLys after addition of CPM and an inhibitor (MGTA, 10 PM).

FIG. 3 illustrates a fluorescence spectrum of 6-fluAFPhe after addition of CPA1 and an inhibitor (potato carboxypeptidase inhibitor, 10 μM).

FIG. 4 illustrates relative fluorescence intensity of 6-fluAFGlu after addition of a cell lysate and an inhibitor (2-PMPA, 10 μM).

FIG. 5 illustrates the relative fluorescence intensity of 6-fluAFGlu after addition of cultured cells and an inhibitor (2-PMPA, 10 μM).

FIG. 6 illustrates a result of measuring a change in fluorescence intensity over time by reacting 6-fluAFLys (Compound 26) with a PBS solution of a lysate of MDCK cells.

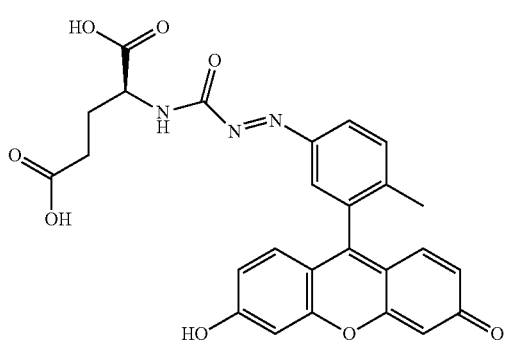

FIG. 7 illustrates a result of live cell imaging of 6-FDAAFLys (Compound 24) using MDCK cells.

FIG. 8 illustrates a result of live cell imaging of 6-FDAAFLys (Compound 24) using the MDCK cells.

FIG. 9 illustrates an absorption spectrum of 2Me5GluAF-TG (Compound 32).

FIG. 10 illustrates a fluorescence spectrum of 2Me5GluAF-TG (Compound 32).

FIG. 11 illustrates a change in fluorescence intensity associated with an enzymatic reaction of 2Me5GluAF-TG.

FIG. 12 is a diagram plotting a fluorescence increase rate at an initial stage of reaction when PSMA is added to 2Me5GluAF-TG (Compound 32) solutions of various concentrations.

FIG. 13 illustrates results of LC-UV/MS analysis of a solution after a reaction of Recombinant human PSMA with 2Me5GluAF-TG (Compound 32) for 10 hours, and 2Me5GluAF-TG, 2MeTG.

FIG. 14 illustrates results of LC-UV/MS analysis of the solution after the reaction of Recombinant human PSMA with 2Me5GluAF-TG (Compound 32) for 10 hours, and 2Me5GluAF-TG, 2MeTG.

FIG. 15 illustrates a result of examining a reactivity of 2Me5GluAF-TG (Compound 32) with the cell lysate.

FIG. 16 illustrates a result of live cell imaging of 2Me5GluAF-TG using LNCaP cells.

FIG. 17 illustrates a result of live cell imaging of 2Me5GluAF-TG using PC3 cells.

FIG. 18a illustrates a result of live cell imaging of Me5GluAF-TG when the inhibitor (2-PMPA) is added.

FIG. 18b illustrates a result of live cell imaging of Me5GluAF-TG when the inhibitor (2-PMPA) is added.

FIG. 19 illustrates a result obtained when, after imaging of LNCaP cells using 2Me5GluAF-TG, a collected extracellular fluid, 2Me5GluAF-TG and 2MeTG are subjected to LC-MS analysis.

FIG. 20 illustrates a result obtained when, after imaging of the LNCaP cells using 2Me5GluAF-TG, the collected extracellular fluid, 2Me5GluAF-TG and 2MeTG are subjected to the LC-MS analysis.

FIG. 21 illustrates a result of a study using a human prostate cancer surgical specimen of 2Me5GluAF-TG.

FIG. 22 illustrates a result of a study using a human prostate cancer surgical specimen of 2Me5GluAF-TG.

FIG. 23 illustrates a result of a study using a human prostate cancer surgical specimen of 2Me5GluAF-TG.

FIG. 24 illustrates a result of a study using a human prostate cancer surgical specimen of 2Me5GluAF-TG.

FIG. 25 illustrates a result of a study using the human prostate cancer surgical specimen of 2Me5GluAF-TG.

FIG. 26 illustrates a total result of an increase rate of the fluorescence intensity after 30 minutes, 60 minutes, and 240 minutes of each site subjected to specimen imaging.

DETAILED DESCRIPTION

In the present specification, unless otherwise noted, "alkyl group" or an alkyl moiety of a substituent (e.g., alkoxy group) containing the alkyl moiety refers to an alkyl group including a straight chain, branched chain, ring, or combination thereof having, for example, carbon atoms of 1 to 6, preferably carbon atoms of 1 to 4, more preferably carbon atoms of about 1 to 3. More specifically, examples of the alkyl group include a methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group.

In the present specification, the term "halogen atom" may be a fluorine atom, chlorine atom, bromine atom, or iodine atom, and is preferably a fluorine atom, chlorine atom, or bromine atom.

One embodiment of the present invention is a compound represented by the following general formula (I), or salt thereof.

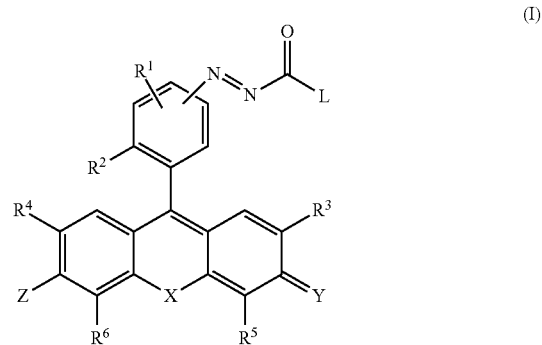

In general formula (I), $R^1$ is a hydrogen atom or represents one to three monovalent substituent groups present on a benzene ring, which are the same or different.

The type of monovalent substituent group represented by $R^1$ is not particularly limited; preferred examples may be selected from the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, a hydroxy group, a carboxy group, a sulfonyl group, an alkoxycarbonyl group, a halogen atom, an amino group, an amido group and an alkylamido group.

These monovalent substituent groups may furthermore have any of one or more substituent groups. For example, one or more halogen atoms, carboxy groups, sulfonyl groups, hydroxy groups, amino groups, alkoxy groups, or the like may be present in the alkyl group represented by $R^1$, and, for example, the alkyl group represented by $R^1$ may be an alkyl halide group, a hydroxyalkyl group, a carboxyalkyl group, an aminoalkyl group, or the like. Also, one or two alkyl groups may be present in the amino group represented by $R^1$, and the amino group represented by $R^1$ may be a monoalkyl amino group or a dialkyl amino group.

Furthermore, in the case that the alkoxy group represented by $R^1$ has a substituent group, examples thereof include a carboxy-substituted alkoxy group and an alkoxycarbonyl-substituted alkoxy group, and more specific examples include a 4-carboxybutoxy group and a 4-acetoxymethyloxycarbonylbutoxy group.

In a preferred aspect of the present invention, each $R^1$ is a hydrogen atom.

In general formula (I), $R^2$ represents a monovalent substituent group present on a benzene ring.

The monovalent substituent of $R^2$ is preferably selected from an alkyl group having 1 to 6 carbon atoms, a hydroxyalkyl group having 1 to 6 carbon atoms, an alkoxy group having 1 to 6 carbon atoms, an aminoalkyl group having 1 to 6 carbon atoms, a carboxyl group, an alkoxycarbonyl group, an amide group and a carboxamide group which may have a substituent on the nitrogen, and more preferably selected from alkyl having 1 to 6 carbon atoms and an alkoxy group having 1 to 6 carbon atoms. Though not intending to be bound by theory, if $R^2$ is alkyl having 1 to 6 carbon atoms or an alkoxy group having 1 to 6 carbon atoms, which is a hydrophobic group, after the compound of the present invention changes to a fluorescent substance on a cell membrane, a cell membrane permeability increases, so that the substance is easily taken up into cells and can be suitably used for live cell imaging.

When $R^2$ represents an alkyl group, one or more halogen atoms, sulfonyl groups, alkoxy groups, or the like may be present in the alkyl group.

In general formula (I), $R^3$ and $R^4$ are, each independently, a hydrogen atom, an alkyl group having 1 to 6 carbon atoms, or a halogen atom.

When $R^3$ or $R^4$ represents an alkyl group, one or more halogen atoms, carboxy groups, sulfonyl groups, hydroxy groups, amino groups, alkoxy groups, or the like may be present in the alkyl group, and, for example, the alkyl group represented by $R^3$ or $R^4$ may be an alkyl halide group, a hydroxyalkyl group, a carboxyalkyl group, or the like. $R^3$ and $R^4$ are, each independently, preferably a hydrogen atom or a halogen atom, and it is more preferable that $R^3$ and $R^4$ both be hydrogen atoms, or $R^3$ and $R^4$ both be fluorine atoms or chlorine atoms.

In general formula (I), $R^5$ and $R^6$ are, each independently, a hydrogen atom, an alkyl group having 1 to 6 carbon atoms, or a halogen atom. The details of $R^5$ and RE are the same as those described for $R^3$ and $R^4$. $R^5$ and $R^6$ are preferably both hydrogen atoms, both chlorine atoms, or both fluorine atoms.

In general formula (I), X is selected from an oxygen atom, $Si(R^a)(R^b)$, $C(R^a)(R^b)$, $Ge(R^a)(R^b)$, $P(=O)R^c$ or Se.

In a preferred aspect of the present invention, X is an oxygen atom.

$R^a$ and $R^b$ are, each independently, an alkyl group having 1 to 6 carbon atoms or an aryl group optionally being substituted. $R^a$ and $R^b$ are, each independently, preferably an alkyl group having 1 to 3 carbon atoms, and it is more preferable that $R^a$ and $R^b$ both be methyl groups.

One or more halogen atoms, carboxy groups, sulfonyl groups, hydroxy groups, amino groups, alkoxy groups, or the like may be present in the alkyl group represented by $R^a$ and $R^b$, and, for example, the alkyl group represented by $R^a$ and $R^b$ may be an alkyl halide group, a hydroxyalkyl group, a carboxyalkyl group, or the like.

When $R^a$ and $R^b$ represent an aryl group, the aryl group may be a monocyclic aromatic group or condensed aromatic group, and the aryl ring may include one or more ring-constituting heteroatoms (e.g., nitrogen atom, oxygen atom, sulfur atom, or the like). A phenyl group is preferred as the aryl group. One or more substituent groups may be present on the aryl ring. One or more substituent groups such as a halogen atom, carboxy group, sulfonyl group, hydroxy group, amino group, alkoxy group, or the like may be present.

$R^c$ is an alkyl group having 1 to 6 carbon atoms or a phenyl group optionally being substituted. Examples of the substituent of the phenyl group include a methyl group, a hydroxy group and a methoxy group.

From the viewpoint of easy introduction in synthesis, $R^c$ is preferably a methyl group or a phenyl group. It is more preferable that $R^C$ be a methyl group because water solubility is higher.

In general formula (I), Y and Z are selected from a pair of (O, OH), ($NR^7R^8$, $NR^9R^{10}$), or (O, $NR^9R^{10}$).

When Y and Z are O and OH, respectively, general formula (I) can be represented as follows.

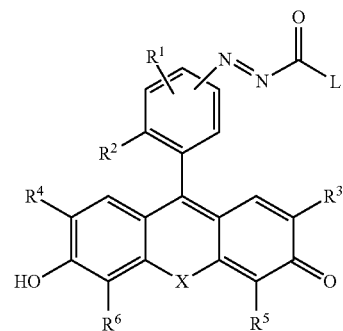

When Y and Z are $NR^7R^8$ and $NR^9R^{10}$, respectively, general formula (I) can be represented as follows.

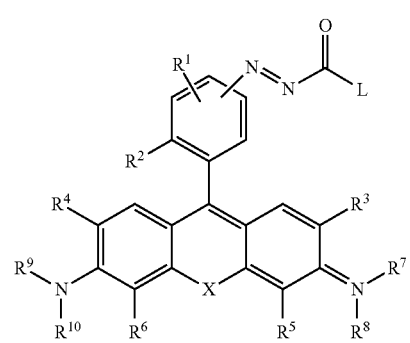

When Y and Z are O and $NR^9R^{10}$, respectively, general formula (I) can be represented as follows.

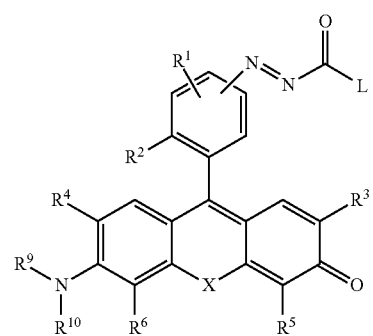

Here, $R^7$ and $R^8$ are, each independently, a hydrogen atom or an alkyl group having 1 to 3 carbon atoms.

$R^7$ and $R^8$ together may form a 4-7 membered heterocyclyl containing a nitrogen atom to which $R^7$ and $R^8$ are bonded.

$R^7$ or $R^8$, or both $R^7$ and $R^8$, together with $R^3$ and/or $R^5$, respectively, may form a 5-7 membered heterocyclyl or heteroaryl containing a nitrogen atom to which $R^7$ and/or $R^8$ are bonded. The heterocyclyl or heteroaryl may contain from one to three heteroatoms selected from the group consisting of an oxygen atom, nitrogen atom, and sulfur atom as ring-constituting members, and the heterocyclyl or heteroaryl may be substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms.

$R^9$ and $R^{10}$ are, each independently, a hydrogen atom or an alkyl group having 1 to 3 carbon atoms.

$R^9$ and $R^{10}$ together may form a 4-7 membered heterocyclyl containing a nitrogen atom to which $R^9$ and $R^{10}$ are bonded.

$R^9$ or $R^{10}$, or both $R^9$ and $R^{10}$, together with $R^4$ and/or $R^6$, respectively, may form a 5-7 membered heterocyclyl or heteroaryl containing a nitrogen atom to which $R^9$ and/or $R^{10}$ are bonded. The heterocyclyl or heteroaryl may contain from one to three heteroatoms selected from the group consisting of an oxygen atom, nitrogen atom, and sulfur atom as ring-constituting members, and the heterocyclyl or heteroaryl may be substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms.

When Y and Z are O and OH, respectively, and when a monovalent substituent group present on a benzene ring of $R^2$ is a carboxyl group, Y and Z may be acetylated. That is, when the monovalent substituent group present on the benzene ring of $R^2$ is a carboxyl group, Y and Z may be (AcO, AcO) (Ac represents an acetyl group). In this case, general formula (I) can be represented as follows.

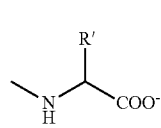

(V)

In general formula (I), L represents an amino acid residue.

L in general formula (I) can be represented by the following formula.

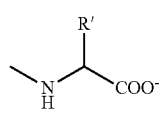

(1)

In formula (I), R' represents a side chain of an amino acid.

In this case, a compound of general formula (I) can be represented by the following general formula (Ia).

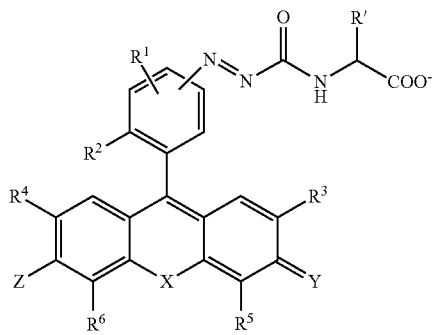

(Ia)

R' represents a side chain of an amino acid.

The amino acid residue of L is selected from residues of arbitrary amino acids. Examples of the amino acid include leucine, isoleucine, valine, lysine, threonine, arginine, asparagine, aspartic acid, glutamine, glutamic acid, serine, histidine, phenylalanine, alanine, glycine, tryptophan, tyrosine, cysteine, histidine, methionine, proline, ornithine, N-methylleucine, 2,3-diaminopropanoic acid, 2,4-diaminobutyric acid, ornithine, and α-hydroxyleucine.

In the present invention, the amino acid residue of L is preferably a phenylalanine residue, a leucine residue, a glutamic acid residue, a glutamine residue, an arginine residue or a lysine residue.

One feature of the present invention is to introduce an azoamide group, showing a spontaneous decarboxylation/denitrification reaction with hydrolysis of a substrate amino acid, with respect to a skeleton of a fluorescent dye such as fluorescein or rhodamine. As a result, it is possible to provide a fluorescent probe applicable to any general carboxypeptidase activity capable of being detected with high sensitivity while suppressing the number of reaction points with carboxypeptidase to one.

Though not intending to be bound by theory, amino acid is cleaved from the compound of general formula (I) in which the amino acid used as a substrate by each carboxypeptidase is condensed with an azoamide group by an enzymatic reaction, and the subsequent decarboxylation/denitrification reaction spontaneously occurs, whereby a fluorescent dye such as fluorescein is generated. While the fluorescent probe before the reaction exists in a weak fluorescent state due to photoinduced electron transfer, the fluorescent dye such as fluorescein as a reaction product has a strong fluorescence, so that an increase in fluorescence can be observed by the enzymatic reaction.

Though not intending to be bound by theory, general formula for the reaction of a compound of the present invention (according to general formula (Ia)) with carboxypeptidase is shown below.

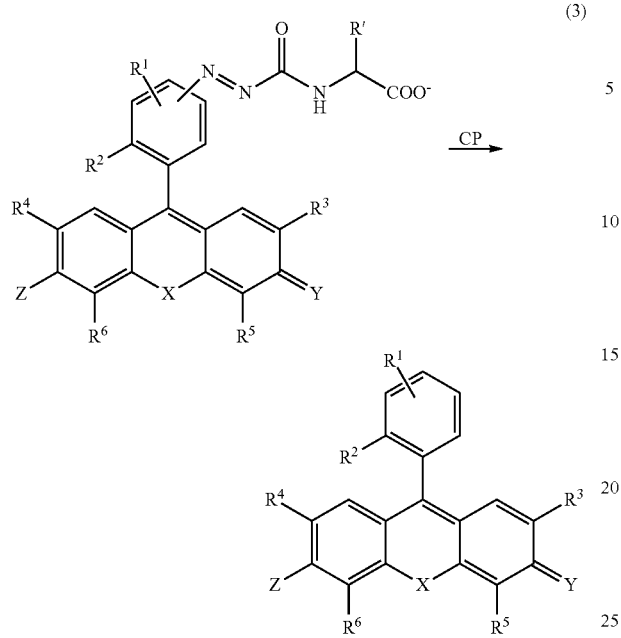

Although the azoamide group condensed with the amino acid represented by the following formula in general formula (I) can be introduced at any position of the benzene ring, depending on the type of carboxypeptidase, the azoamide group is easily reacted depending on the introduction position of the azoamide group condensed with the amino acid into the benzene ring, so that it is preferable that the azoamide group be introduced at a meta position or a para position with respect to R². Here, in general formula (I), when the compound has a carboxy group as R², the meta position is referred to as the 5-position, and the para position is referred to as the 6-position. When the compound has a substituent other than the carboxy group as R², the meta position is referred to as the 4-position, and the para position is referred to as the 5-position.

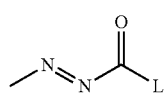

(2)

The followings are non-limiting examples of the compound of general formula (I) of the present invention.

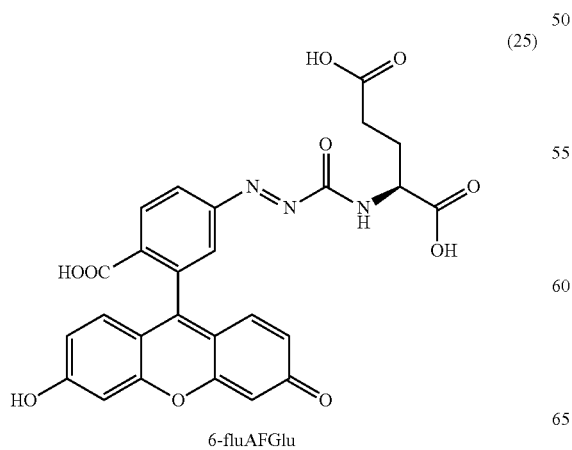

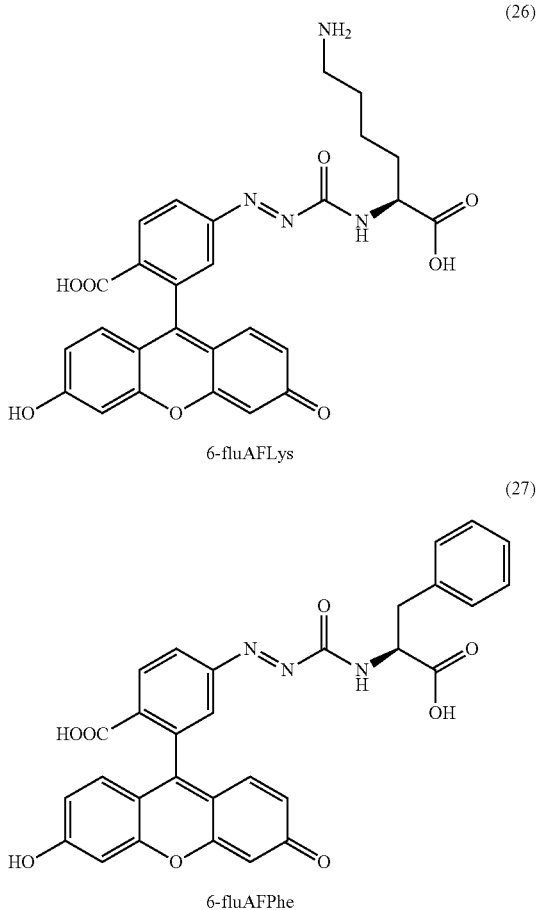

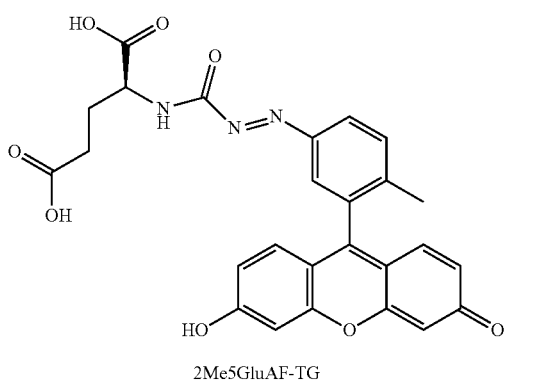

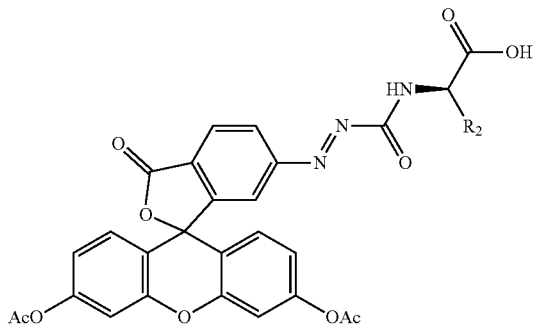

(R₂ is CH₂CH₂COOH or CH₂CH₂CH₂CH₂NH₂)

While not intending to limit the scope of the invention, as shown in the examples below, 6-fluAFGlu (Compound 25) can function as a probe for a prostate-specific membrane antigen (PSMA) using glutamic acid as a substrate, 6-fluAFLys (Compound 26) can function as a probe for carboxypeptidase M (CPM) using a basic amino acid as a substrate, and 6-fluAFPhe (Compound 27) can function as a probe for carboxypeptidase A (CPA) using bulky amino acid as a substrate.

The compound of general formula (I) of the present invention can exist as an acid addition salt or a base addition salt. Examples of the acid addition salt include mineral acid salts such as hydrochlorides, sulfates and nitrates, and organic acid salts such as methanesulfonate, p-toluenesulfonate, oxalate, citrate and tartrate. Examples of the base addition salt include metal salts such as sodium salt, potassium salt, calcium salt and magnesium salt, ammonium salt, and organic amine salts such as triethylamine salt. In addition to these, there are also cases in which salts form with an amino acid such as glycine. Compounds or salts thereof of general formula (I) of the present invention can also exist as hydrates or solvates, but these substances are also within the scope of the present invention.

The compound of general formula (I) of the present invention sometimes has one or more asymmetrical carbons, depending on the types of substituents. In addition to optical isomers based on one or more asymmetrical carbons and stereoisomers such as diastereomers based on two or more asymmetrical carbons, any mixtures of stereoisomers, racemates, etc., are all encompassed within the scope of the present invention.

Methods for producing representative compounds of compounds of general formula (I) of the present invention are specifically shown in the examples in the present specification. Therefore, one skilled in the art can produce compounds represented by general formula (I) by appropriately selecting the reaction raw materials, reaction conditions, reaction reagents, etc. based on these explanations and modifying or changing these methods as needed.

One more embodiment of the present invention is a fluorescent probe for detecting carboxypeptidase activity that includes the compound of general formula (I) or salt thereof.

The fluorescent probe for detecting carboxypeptidase activity of the present invention can be applied to detection of a wide range of carboxypeptidases. For example, the fluorescent probe can be applied to carboxypeptidase A, carboxypeptidase B, carboxypeptidase M, prostate-specific membrane antigen (PSMA) using glutamic acid as a substrate, and the like.

One more embodiment of the present invention is a method of detecting carboxypeptidase in a cell, wherein the method includes (a) introducing the fluorescent probe of the present invention into the cell and (b) measuring fluorescence emitted in the cell by the fluorescent probe.

One more embodiment of the present invention is a method of detecting a prostate cancer, wherein the method comprises (a) applying the fluorescent probe of the present invention to a clinical specimen of prostate and (b) measuring a fluorescence image of a surgical specimen of the prostate to which the fluorescent probe is applied.

In order to apply the fluorescent probe of the present invention in the step (a) to the clinical specimen of prostate, for example, a solution of the fluorescent probe of the present invention (e.g., diluted with 1×TBS buffer, the concentration is about 50 μM) is added dropwise so that the whole specimen is immersed in the solution. It is preferable to wash the clinical specimen with 1×TBS buffer or the like before applying the fluorescent probe of the present invention.

Examples of clinical specimens include surgical specimens of prostate cancer.

By measuring the fluorescence image of the clinical specimen of prostate to which the fluorescent probe of the present invention is applied, it is possible to determine that a site showing bright fluorescence has a high cancer rate. In this case, it may be determined that the cancer rate is high when the fluorescence intensity itself is high. However, preferably, the fluorescent probe of the present invention is applied, and using an increase rate of the fluorescence intensity after a lapse of certain time (e.g., 30 minutes, 60 minutes, etc.) as an index, it is possible to determine that a site having a high increase rate has a high cancer rate.

In the method of detecting prostate cancer according to the present invention, when a compound in which $R^2$ is alkyl having 1 to 6 carbon atoms or an alkoxy group having 1 to 6 carbon atoms is used among the fluorescent probes of the present invention, the probe is more easily taken up into cells, and prostate cancer can be detected more effectively, which is preferable.

The method of using the fluorescent probe of the present invention is not particularly limited, and the fluorescent probe can be used in the same manner as conventionally known fluorescent probes. Usually, the compound represented by general formula (I) or salt thereof may be dissolved in an aqueous medium such as physiological saline and buffer, a mixture of the aqueous medium and a water-miscible organic solvent such as ethanol, acetone, ethylene glycol, dimethyl sulfoxide, and dimethylformamide, or the like, this solution may be added to an appropriate buffer containing cells or tissues, and fluorescence spectrum may be measured. The fluorescent probe of the present invention may be combined with an appropriate additive and used in the form of a composition. For example, it may optionally be combined with additives such as buffers, dissolving aids, and pH adjusting agents.

EXAMPLES

Hereinafter, the present invention is described by Examples, but the present invention is not limited thereto.

Synthesis Example 1

According to the following scheme 1, 5-fluAFGlu (Compound 13), 6-fluAFGlu (Compound 25), 6-fluAFLys (Compound 26) and 6-fluAFPhe (Compound 27), which are fluorescent probes for detecting carboxypeptidase activity of the present invention, were synthesized.

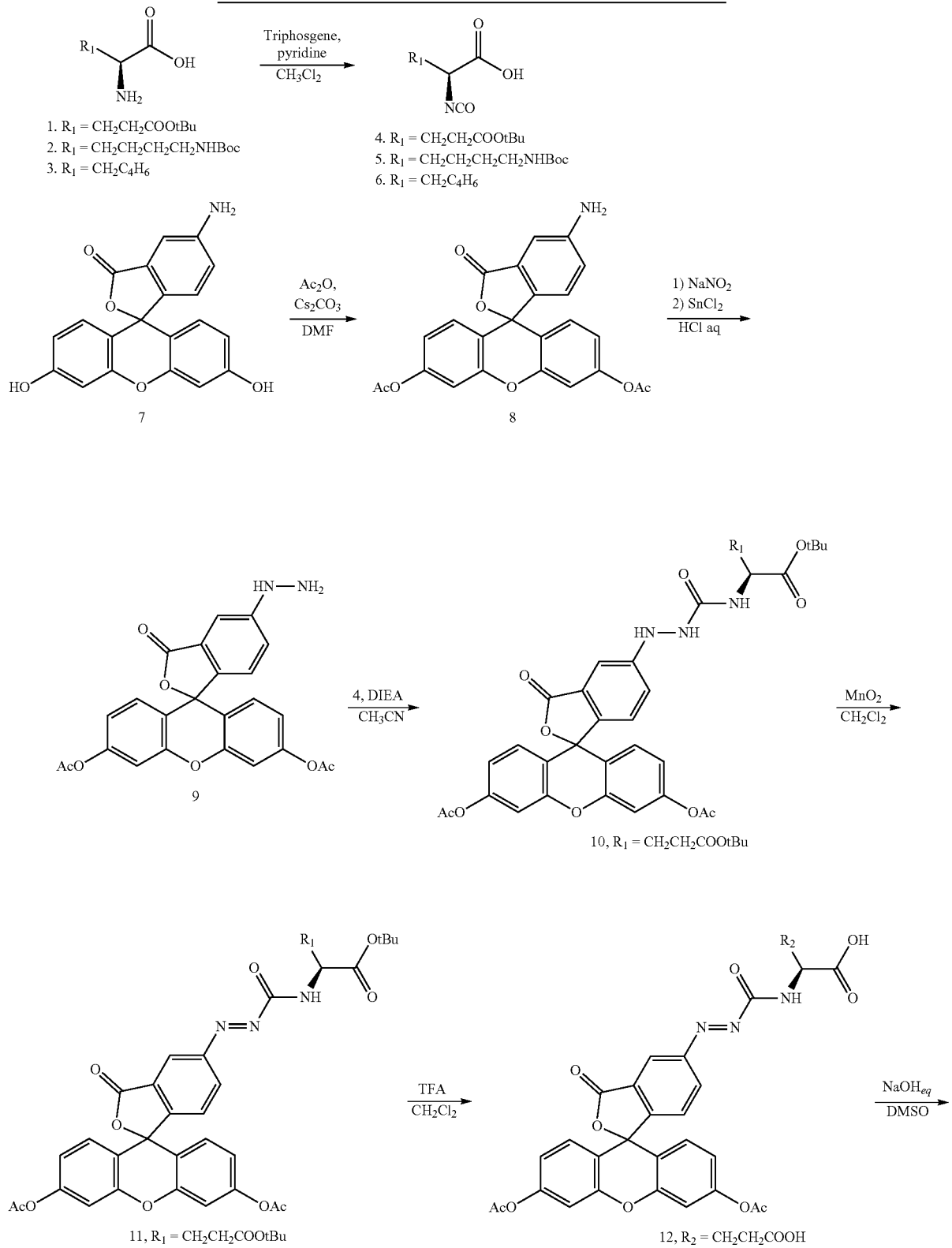

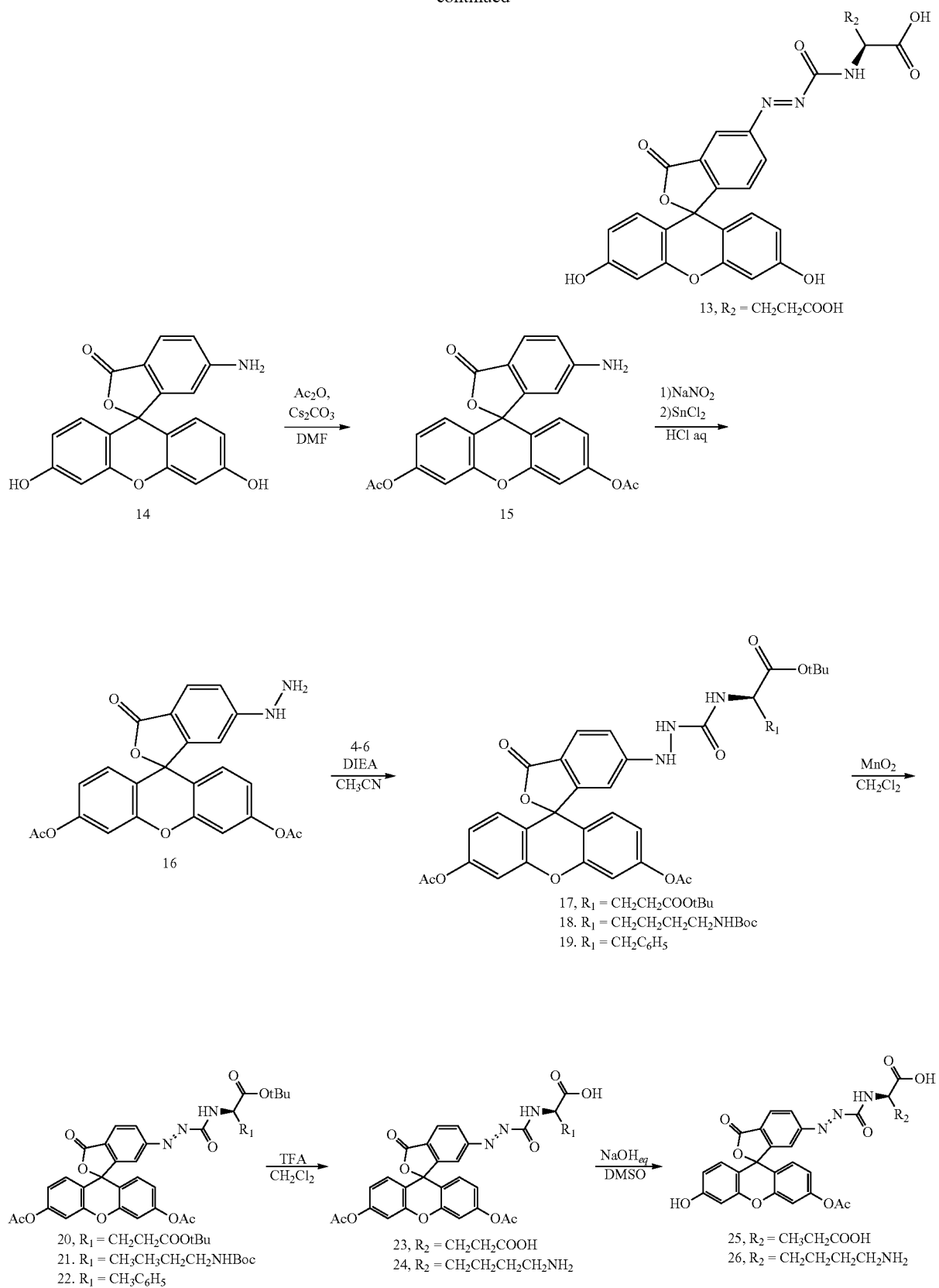

-continued

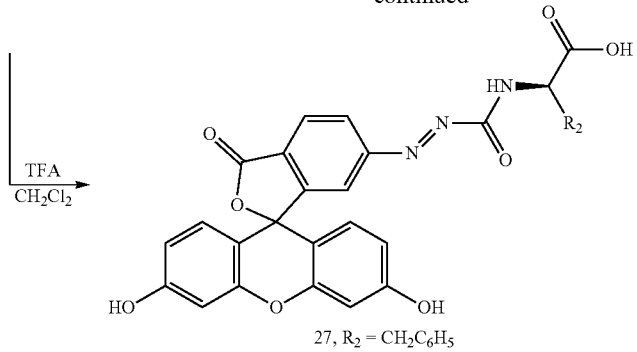

27, $R_2 = CH_2C_6H_5$

(1) Synthesis of Compound 4

A dichloromethane solution (45 mL) of H-Glu(OtBu)-OtBu hydrochloride (Compound 1) (1.3 g, 4.4 mmol, 1 eq) and pyridine (250 μL) was cooled to −10° C., a dichloromethane solution (5 mL) of triphosgene (860 mg, 3 mmol, 0.67 eq) was added, and the mixture was stirred under an argon atmosphere at −10° C. for 2 hr. A 0.1 N hydrochloric acid aqueous solution was added, the mixture was extracted with dichloromethane, washed with saturated saline, and then dried with sodium sulfate, and the solvent was removed under reduced pressure to obtain a target compound (Compound 4) as a transparent liquid. The target product was directly used for the next reaction without further purification.

HRMS after derivatization by methanol (ESI+) m/z calcd. for $[M+Na]^+$, 340.1737; found, 347.1731 (−0.6 mmu).

(2) Synthesis of Compound 5

A dichloromethane solution (15 mL) of H-Lys(Boc)-OtBu hydrochloride (Compound 2) (691 mg, 2.0 mmol, 1 eq) and pyridine (400 μL) was cooled to −10° C., a dichloromethane solution (2 mL) of triphosgene (395 mg, 1.3 mmol, 0.67 eq) was added, and the mixture was stirred under an argon atmosphere at −10° C. for 30 minutes. A 0.1 N hydrochloric acid aqueous solution was added, the mixture was extracted with dichloromethane, washed with saturated saline, and then dried with sodium sulfate, and the solvent was removed under reduced pressure to obtain a target compound (Compound 5) as a transparent liquid. The target product was directly used for the next reaction without further purification.

(3) Synthesis of Compound 6

A dichloromethane solution (10 mL) of H-Phe-OtBu hydrochloride (Compound 3) (155 mg, 0.6 mmol, 1 eq) and pyridine (100 μL) was cooled to −10° C., triphosgene (120 mg, 0.4 mmol, 0.67 eq) was added, and the mixture was stirred under an argon atmosphere at −10° C. for about 1 hr. A 0.1 N hydrochloric acid aqueous solution was added, the mixture was extracted with dichloromethane, washed with saturated saline, and then dried with sodium sulfate, and the solvent was removed under reduced pressure to obtain a target compound (Compound 6) as a transparent liquid. The target product was directly used for the next reaction without further purification.

(4) Synthesis of Compound 8

5-aminofluorescein (Compound 7) (1.92 g, 5.5 mmol, 1 eq) and cesium carbonate (3.97 g, 12.1 mmol, 2.2 eq) were dissolved in a 10 mL DMF solution, acetic anhydride (1.14 mL, 12.1 mmol, 2.2 eq) was added dropwise, and the mixture was stirred at room temperature for 1 hour. After the solvent was removed under reduced pressure, water was added, and the mixture was extracted with dichloromethane, washed with saturated saline, and then dried with sodium sulfate. The solvent was removed under reduced pressure to obtain a target crude product as a yellow oily substance. Subsequently, the product was purified by silica gel column chromatography (n-hexane/ethyl acetate) to obtain a target compound (Compound 8) (1.94 g, 81%) as a white solid.

$^1$H NMR (400 MHz, CDCl$_3$): δ 7.20 (d, J=2.0 Hz, 1H), 7.07 (d, J=2.3 Hz, 2H), 6.92-6.89 (m, 3H), 6.85 (d, J=8.2 Hz, 1H), 6.81 (d, J=2.3, 8.7 Hz, 2H), 2.29 (s, 6H); $^{13}$C NMR (101 MHz, CDCl$_3$): δ 169.6, 168.9, 151.8, 151.5, 149.0, 141.6, 129.0, 127.4, 124.4, 122.4, 117.5, 117.1, 110.1, 108.2, 81.6, 20.9; HRMS (ESI+) m/z calcd. for $[M+Na]^+$, 454.0897; found, 454.0888 (−0.9 mmu).

(5) Synthesis of Compound 10

Compound 8 (400 mg, 0.9 mmol, 1 eq) was dissolved in concentrated hydrochloric acid (12 N HCl$_{aq}$) (2 mL) cooled to 4° C., a sodium nitrite (NaNO$_2$) (96 mg, 1.4 mmol, 1.5 eq) solution (2 mL) was slowly added dropwise under an ice bath, and the mixture was stirred under an ice bath for 30 minutes. After the consumption of raw materials was confirmed, a dilute hydrochloric acid (1N HCl$_{aq}$) solution (2 mL) of tin chloride II (SnCl$_2$) (265 mg, 1.4 mmol, 1.5 eq) was slowly added dropwise under an ice bath, and the mixture was stirred under an ice bath for another 15 minutes. Then, a saturated aqueous sodium hydrogencarbonate solution was slowly added dropwise for neutralization, and then the mixture was extracted with ethyl acetate, washed with saturated saline, and then dried with sodium sulfate. The solvent was removed under reduced pressure to obtain a yellow oily synthetic intermediate (Compound 9) as a crude product. Subsequently, the synthetic intermediate was dissolved in acetonitrile (CH$_3$CN), and then N,N-diisopropylethylamine (DIEA) (314 μL, 1.8 mmol, 2 eq) and a crude product of Compound 4 (1.1 mmol, 1.2 eq) were added. The mixture was stirred at room temperature for 1 hour. A 0.1 N hydrochloric acid aqueous solution was added to a reaction solution, the mixture was extracted with dichloromethane, washed with saturated saline, and then dried with sodium sulfate, and the solvent was removed under reduced pressure to obtain a crude object product as a yellow liquid. After crude purification by silica gel column chromatography (n-hexane/ethyl acetate), re-purification was performed by high performance liquid chromatography (HPLC), and the solvent was removed by freeze-drying to obtain a target compound (Compound 10) (25.7 mg, 4%) as a yellow solid. 1H NMR (400 MHz, CD$_3$OD): δ 7.38 (d, J=2.0 Hz, 1H), 7.26 (dd, J=2.2 Hz, 8.4 Hz, 1H), 7.16 (dd, J=0.7 Hz, 2.0 Hz, 2H), 7.05 (d, J=8.4 Hz, 1H), 6.89-6.88 (m (br), 4H), 4.31-4.28 (dd, J=4.8 Hz, 9.6 Hz, 1H), 2.38-2.29 (m, 8H), 2.16-2.07 (m, 1H), 1.94-1.84 (m, 1H), 1.46 (s, 9H), 1.43 (s, 9H); $^{13}$C NMR (101 MHz, CD$_3$OD): δ 173.9, 173.1, 171.2, 170.5, 153.8, 152.9, 130.0, 128.5, 125.6, 122.2, 119.2, 118.1, 111.5, 107.4, 83.1, 83.0, 81.8, 54.2, 32.6, 28.4, 28.3, 28.2, 20.9; HRMS (ESI+) m/z calcd. for [M+Na]$^+$, 754.2582; found, 754.2595 (1.3 mmu).

(6) Synthesis of Compound 12

Compound 10 (25 mg, 0.034 mmol, 1 eq) was dissolved in dichloromethane, manganese dioxide (MnO$_2$) (250 mg, 2.87 mmol, 84 eq) was added thereto, and the mixture was stirred at room temperature for 10 minutes. The reaction suspension was filtered to obtain a dichloromethane solution of a yellow synthetic intermediate (Compound 11). Subsequently, trifluoroacetic acid (TFA) was added to a filtrate, and the mixture was stirred at room temperature for 6 hours. The solvent was removed under reduced pressure to obtain a crude object product as a yellow solid. The crude product was repurified by high performance liquid chromatography (HPLC), and the solvent was removed by freeze-drying to obtain a target compound (Compound 12) (6 mg, 29%) as a yellow solid.

$^1$H NMR (400 MHz, CD$_3$OD): δ 9.26 (d, J=8.1 Hz, 1H), 8.55 (d, J=1.3 Hz, 1H), 8.31 (dd, J=1.6 Hz, 8.0 Hz, 1H), 7.47 (dd, J=0.5 Hz, 8.2 Hz, 1H), 7.22 (d, J=2.1 Hz, 2H), 6.98 (d, J=8.7 Hz, 2H), 6.93 (dd, J=2.2 Hz, 8.7 Hz, 2H), 4.64-4.60 (m, 1H), 2.55-2.51 (m, 2H), 2.38-2.35 (m, 1H), 2.23 (s, 6H), 2.16-2.12 (m, 1H); $^{13}$C NMR (101 MHz, CD$_3$OD): δ 176.1, 174.0, 170.5, 169.6, 163.6, 157.9, 154.3, 154.1, 152.8, 131.7, 130.1, 128.9, 126.7, 121.2, 119.5, 117.0, 111.7, 83.3, 54.4, 31.2, 27.8, 20.9; HRMS (ESI+) m/z calcd. for [M+Na]$^+$, 640.1174; found, 640.1172 (−0.2 mmu).

(7) Synthesis of 5-fluAFGlu (Compound 13)

Compound 12 (1.8 mg, 0.003 mmol) was dissolved in DMSO, a 0.01N aqueous sodium hydroxide solution (NaOHaq) was added thereto, and the mixture was stirred at room temperature for 30 minutes. After the reaction solution was acidified with dilute hydrochloric acid (1N HClaq), purification was performed by high performance liquid chromatography (HPLC), and the solvent was removed by freeze-drying to obtain a target compound 5-fluAFGlu (Compound 13) (1.7 mg, quant) as a yellow solid.

$^1$H NMR (400 MHz, CD$_3$OD): δ 8.58 (d, J=1.2 Hz, 1H), 8.33 (dd, J=1.8 Hz, 8.2 Hz, 1H), 7.48 (d, J=8.2 Hz, 1H), 6.83 (br, 4H), 6.69 (d, J=8.8 Hz, 2H), 4.62 (dd, J=4.9 Hz, 9.2 Hz, 1H), 2.56-2.52 (m, 2H), 2.42-2.33 (m, 1H), 2.19-2.11 (m, 1H); HRMS (ESI+) m/z calcd. for [M+Na]$^+$, 556.0963; found, 556.0965 (0.2 mmu).

(8) Synthesis of Compound 15

6-aminofluorescein (Compound 14) (1.05 g, 3 mmol, 1 eq) was used as a starting material, and synthesis was performed by the same protocol as in the synthesis of Compound 8 to obtain a target compound (15) (1.38 g, qunat.) as a yellow solid.

$^1$H NMR (400 MHz, CDCl$_3$): δ 7.74 (d, J=8.4 Hz, 1H), 7.04 (d, J=2.3 Hz, 2H), 6.95 (d, J=8.6 Hz, 2H), 6.81 (dd, J=2.3 Hz, 8.6 Hz, 2H), 6.75 (dd, J=2.0, 8.3 Hz, 1H), 6.22 (d, J=2.0 Hz, 1H), 2.31 (s, 6H); $^{13}$C NMR (101 MHz, CDCl$_3$): δ 169.6, 169.1, 156.4, 153.3, 151.9, 151.4, 129.2, 126.9, 117.8, 117.2, 116.6, 115.0, 110.3, 107.6, 80.3, 21.3; HRMS (ESI+) m/z calcd. for [M+Na]$^+$, 454.0897; found, 454.0888 (−0.9 mmu).

(9) Synthesis of Compound 17

Compound 15 (470 mg, 1.1 mmol, 1 eq) was dissolved in concentrated hydrochloric acid (12 N HCl$_{aq}$) (2 mL) cooled to 4° C., a sodium nitrite (NaNO$_2$) (110 mg, 1.6 mmol, 1.5 eq) solution (2 mL) was slowly added dropwise under an ice bath, and the mixture was stirred under an ice bath for 30 minutes. After the consumption of raw materials was confirmed, a dilute hydrochloric acid (1N HCl$_{aq}$) solution (2 mL) of tin chloride II (SnCl$_2$) (300 mg, 1.6 mmol, 1.5 eq) was slowly added dropwise under an ice bath, and the mixture was stirred under an ice bath for another 15 minutes. Then, a saturated aqueous sodium hydrogencarbonate solution was slowly added dropwise for neutralization, and then the mixture was extracted with ethyl acetate, washed with saturated saline, and then dried with sodium sulfate. The solvent was removed under reduced pressure to obtain a yellow oily synthetic, intermediate (Compound 16) as a crude product. Subsequently, the synthetic intermediate was dissolved in 10 mL of acetonitrile (CH$_3$CN), and then N,N-diisopropylethylamine (DIEA) (380 μL, 1.8 mmol, 2.2 eq) and a crude product of Compound 4 (1.5 mmol, 1.4 eq) were added. The mixture was stirred at room temperature for 1 hour. After the reaction solution was subjected to crude purification directly by silica gel column chromatography (n-hexane/ethyl acetate), re-purification was performed by high performance liquid chromatography (HPLC), and the solvent was removed by freeze-drying to obtain a target compound (Compound 17) (97.6 mg, 12%) as a yellow solid. 1H NMR (400 MHz, CDCl$_3$): δ 7.83 (d, J=8.5 Hz, 1H), 7.06-7.03 (m, 3H), 6.90 (d, J=6.4 Hz, 1H), 6.88 (d, J=6.4 Hz, 1H), 6.80 (ddd, J=1.3 Hz, 3.2 Hz, 8.6 Hz, 2H), 6.67 (s, 1H), 6.62 (s, 1H), 6.49 (d, J=1.7 Hz, 1H), 6.16 (d, J=8.1 Hz, 1H), 4.27-4.24 (dd, J=4.8, 8.4 Hz, 1H), 2.29 (s, 6H), 2.22-2.15 (m, 2H), 2.03-2.00 (m, 1H), 1.81-1.35 (m, 1H), 1.36 (s, 9H), 1.35 (s, 9H); $^{13}$C NMR (101 MHz, CDCl$_3$): δ 172.4, 171.6, 169.1, 169.0, 158.4, 155.7, 154.4, 152.0, 151.5, 129.1, 127.0, 118.3, 117.8, 116.8, 114.9, 110.4, 106.7, 82.4, 81.0, 80.8, 52.9, 31.6, 28.1, 28.0, 27.7, 21.2; HRMS (ESI+) m/z calcd. for [M+Na]$^+$, 754.2582; found, 754.2585 (0.3 mmu).

(10) Synthesis of Compound 18

Compound 15 (199 mg, 0.45 mmol) was used as a starting material, and synthesis was performed by the same protocol as in the synthesis of Compound 10 to obtain a target compound (Compound 18) (33 mg, 0.043 mmol, 9.6%) as a yellow solid. 1H NMR (400 MHz, CDCl$_3$): δ 7.85 (d, J=8.8 Hz, 1H), 7.06-7.04 (m, 3H), 6.90 (dd, J=1.2 Hz, 8.8 Hz, 2H), 6.81 (dd, J=2.3 Hz, 8.4 Hz, 2H), 6.73 (s, 1H), 6.57 (s, 1H), 6.50 (d, J=1.7 Hz, 1H), 6.01 (d, J=8.2 Hz, 1H), 4.67 (s, 1H), 4.30-4.25 (m, 1H), 3.00-2.95 (m, 2H), 2.30 (s, 6H), 1.98 (s, 2H), 1.78-1.71 (m, 1H), 1.59-1.50 (m, 1H), 1.39 (s, 9H), 1.37 (s, 9H), 1.25-1.21 (m, 2H); $^{13}$C NMR (101 MHz, CDCl$_3$): δ 173.0, 170.1, 170.1, 170.0, 156.9, 155.4, 153.0, 153.0, 152.4, 129.9, 127.8, 119.0, 118.6, 117.6, 117.5, 115.7, 111.0, 107.3, 82.8, 81.2, 53.5, 40.6, 32.4, 29.7, 28.7, 28.2, 22.6, 21.4; HRMS (ESI+) m/z calcd. for [M+H]$^+$, 775.31850; found, 775.31915 (0.7 mmu).

(11) Synthesis of Compound 19

Compound 15 (358 mg, 0.83 mmol, 1 eq) was dissolved in concentrated hydrochloric acid (12 N HCl$_{aq}$) (2 mL) cooled to 4° C., a sodium nitrite (NaNO$_2$) (57 mg, 0.83 mmol, 1 eq) solution (1.5 mL) was slowly added dropwise under an ice bath, and the mixture was stirred under an ice bath for 30 minutes. After the consumption of raw materials was confirmed, a dilute hydrochloric acid (1N HCl$_{aq}$) solution (2 mL) of tin chloride II (SnCl$_2$) (237 mg, 1.24 mmol, 1.5 eq) was slowly added dropwise under an ice bath, and the mixture was stirred under an ice bath for another 10 minutes. Then, a saturated aqueous sodium hydrogencarbonate solution was slowly added dropwise for neutralization, and then the mixture was extracted with ethyl acetate, washed with saturated saline, and then dried with sodium sulfate. The solvent was removed under reduced pressure to obtain a yellow oily synthetic intermediate (16) as a crude product. One-third of this amount was used for the next reaction. The synthetic intermediate (Compound 16) (0.27 mmol, 1 eq) was dissolved in a dichloromethane solution (5 mL) of a crude product (0.5 mmol, 1.9 eq) of Compound 4, and N,N-diisopropylethylamine (DIEA) (130 μL, 0.75 mmol, 2.8 eq) was added. The mixture was stirred at room temperature for 1 hour. A reaction solution was purified directly by silica gel column chromatography (n-hexane/ethyl acetate) to obtain a crude product (113 mg, 59% from Compound 15) of a target compound (Compound 19) as a yellow solid. Compound 19 was used for the next reaction without further purification.

HRMS (ESI+) m/z calcd. for [M+Na]$^+$, 716.2215; found, 716.2213 (−0.2 mmu).

(12) Synthesis of Compound 23

Compound 17 (20 mg, 0.027 mmol, 1 eq) was used as a starting material, and a target compound (Compound 23) (4.6 mg, 27%) was obtained as a yellow solid by the same protocol as in Compound 12.

$^1$H NMR (400 MHz, CD$_3$OD): δ 9.16 (d, J=8.2 Hz, 1H), 8.27-8.26 (m (br), 2H), 7.68 (dd, J=1.0 Hz, 1.0 Hz, 1H), 7.21 (d, J=2.2 Hz, 2H), 6.97 (d, J=8.7 Hz, 2H), 6.91 (dd, J=2.2 Hz, 8.7 Hz, 2H), 4.56-4.51 (m, 1H), 2.46-2.43 (m, 2H), 2.03-2.00 (m, 7H), 2.07-2.01 (m, 1H); $^{13}$C NMR (101 MHz, CD$_3$OD): δ 176.1, 173.9, 170.5, 169.6, 163.4, 157.6, 155.6, 154.1, 152.9, 130.5, 130.1, 127.9, 127.8, 119.5, 118.5, 117.1, 111.7, 83.3, 54.4, 31.1, 27.8, 20.9; HRMS (ESI+) m/z calcd. for [M+Na]$^+$, 640.1174; found, 640.1146 (−2.8 mmu).

(13) Synthesis of Compound 24

Compound 18 (33 mg, 0.043 mmol) was used as a starting material, and synthesis was performed by the same protocol as in the synthesis of Compound 12 to obtain a target compound (Compound 24) (11.5 mg, 0.019 mmol, 44%) via a synthetic intermediate (Compound 21). 1H-NMR (400 MHz, CD$_3$OD): δ 8.27-8.26 (m, 2H), 7.65 (s, 1H), 7.21 (d, J=2.2, 2H), 6.97 (d, J=8.7, 2H), 6.91 (dd, J=2.2 Hz, 8.7 Hz, 2H), 4.48 (s, 1H), 2.90 (t, J=7.1 Hz, 2H), 2.29 (s, 6H), 2.03-2.01 (m, 1H), 1.86-1.83 (m, 1H), 1.71-1.65 (m, 2H), 1.52-1.46 (m, 2H); HRMS (ESI+) Calcd for [M+H]$^+$, 533.16669; Found, 533.16743 (0.7 mmu).

(14) Synthesis of 6-fluAFGlu (Compound 25)

Compound 23 (1.5 mg, 0.003 mmol) was used as a starting material, and a target compound 6-fluAFGlu (Compound 25) (1.4 mg, quant) was obtained as a yellow solid by the same protocol as in Compound 13.

$^1$H NMR (400 MHz, CD$_3$OD): δ 8.2-8.25 (m, 2H), 7.70 (s, 1H), 6.80-6.78 (m, 4H), 6.65 (dd, J=2.0 Hz, 10.8 Hz, 2H), 4.55 (dd, J=4.9 Hz, 9.2 Hz, 1H), 2.48-2.44 (m, 2H), 2.35-2.27 (m, 1H), 2.10-2.03 (m, 1H); $^{13}$C NMR (101 MHz, CD$_3$OD): δ176.2, 174.0, 169.9, 163.4, 162.5, 157.1, 154.7, 154.0, 131.9, 130.6, 128.1, 127.1, 119.7, 114.5, 111.4, 103.6, 71.4, 54.4, 31.1, 27.8; HRMS (ESI+) m/z calcd. for [M+Na]$^+$, 556.0963; found, 556.0957 (−0.6 mmu).

(15) Synthesis of 6-fluAFLys (Compound 26)

Compound 18 (33 mg, 0.043 mmol) was used as a starting material, and a target compound 6-fluAFLys (Compound 26) (4.0 mg, 0.0075 mmol, 18% from Compound 18) was obtained as a yellow solid by the same protocol as in Compounds 12 and 13 via a synthetic intermediate (Compound 24).

$^1$H-NMR (400 MHz, DMSO-d$_6$): δ 12.85 (s, 1H), 10.20 (s, 2H), 8.98 (d, J=8.0 Hz, 1H), 8.25 (d, J=8.0 Hz, 1H), 8.20 (dd, J=1.6 Hz, 8.0 Hz, 1H), 7.62 (s, 2H), 7.49 (d, J=2.8 Hz, 1H), 6.69 (d, J=2.4 Hz, 2H), 6.67 (d, J=8.7 Hz, 2H), 6.56 (dd, J=2.1 Hz, 8.8 Hz, 2H), 4.24-4.18 (m, 1H), 2.77-2.72 (m, 2H), 1.86-1.77 (m, 1H), 1.71-1.62 (m, 1H), 1.56-1.46 (m, 2H), 1.41-1.33 (m, 2H); HRMS (ESI+) Calcd for [M+H]$^+$, 617.18782; Found, 617.18867 (0.9 mmu).

(16) Synthesis of 6-fluAFPhe (Compound 27)

A crude product of Compound 19 (113 mg, 0.034 mmol, 1 eq) was dissolved in 5 mL of dichloromethane, a small amount of manganese dioxide (MnO$_2$) was added, and the mixture was stirred at room temperature for 10 minutes. The reaction suspension was filtered to obtain a dichloromethane solution of a yellow synthetic intermediate (Compound 22). Subsequently, trifluoroacetic acid (TFA) was added to a filtrate, and the mixture was stirred at room temperature for 24 hours. The solvent was removed under reduced pressure to obtain a crude object product as a yellow solid. The crude product was repurified by high performance liquid chromatography (HPLC), and the solvent was removed by freeze-drying to obtain a target compound (Compound 27) (23 mg, 27% from Compound 19) as a yellow solid.

$^1$H NMR (400 MHz, CDCl$_3$): δ 9.11 (d, J=8.4 Hz, 1H), 8.23 (d, J=8.0 Hz, 1H), 8.17 (dd, J=1.6, 8.4 Hz, 1H), 7.50 (dd, J=0.4, 1.6 Hz, 1H), 7.27-7.20 (m, 4H), 7.19-7.17 (m, 1H), 6.70 (d, J=2.4 Hz, 2H), 6.67 (d, J=8.8 Hz, 2H), 6.57 (dd, J=2.4, 8.8 Hz, 2H), 4.51-4.45 (m, 1H), 3.20-3.15 (m, 1H), 2.97-2.91 (m, 1H); $^{13}$C NMR (101 MHz, CDCl$_3$): δ 172.0, 167.8, 162.0, 159.8, 158.2, 155.7, 153.8, 152.0, 137.3, 129.3, 129.2, 129.1, 128.4, 126.8, 126.6, 115.8, 112.8, 109.0, 102.3, 83.6, 55.0, 36.5; HRMS (ESI+) m/z calcd. for [M+H]$^+$, 552.1399; found, 552.1401 (0.2 mmu).

Example 1

Absorption/fluorescence spectrum measurement of fluorescein, 5-fluAFGlu (Compound 13), 6-fluAFGlu (Compound 25), 6-fluAFLys (Compound 26), and 6-fluAFPhe (Compound 27) The results of absorption/fluorescence spectrum measurement revealed that 5-fluAFGlu (Compound 13), 6-fluAFGlu (Compound 25), 6-fluAFLys (Compound 26) and 6-fluAFPhe (Compound 27) had almost no fluorescence under physiological conditions as compared to highly fluorescent fluorescein. The absorption spectrum was measured using UV-2450 (SIMADZU), and the fluorescence spectrum was measured using F-7000 (HITACHI).

Table 1 illustrates spectroscopic properties of fluorescein, 5-fluAFGlu (Compound 13), 6-fluAFGlu (Compound 25), 6-fluAFLys (Compound 26), and 6-fluAFPhe (Compound 27)

TABLE 1

|  | Absorption maximum (nm) | Fluorescence maximum (nm) | Quantum yield |
|---|---|---|---|
| Fluorescein[1] | 489 | 516 | 0.85 |
| 5-fluAFGlu (13)[a] | 494 | 521 | 0.003 |
| 6-fluAFGlu (25)[a] | 494 | 526 | 0.002 |
| 6-fluAFLys (26)[a] | 494 | 518 | 0.002 |
| 6-fluAFPhe (27)[a] | 494 | 519 | 0.025 |

[a]measured with 200 mM phosphate buffer (pH 7.4)

Example 2

Enzyme Assay

When PSMA was applied to 5-fluAFGlu (Compound 13) and 6-fluAFGlu (Compound 25), only in 6-fluAFGlu, a fluorescence rise due to an enzymatic reaction was observed. A change in the fluorescence spectrum due to the enzymatic reaction was measured as follows. The reactivity of 6-fluAFGlu to PSMA was evaluated by creating a Michaelis-Menten plot.

(1) Two solutions prepared by dissolving 10 μM probe in 200 μL of each assay buffer were provided.
(Assay buffer: 50 mM HEPES, 100 mM NaCl, pH 7.5)
(2) 0.44 μg of PSMA was added to each and incubated at 37° C. for 15 hours. For one of the solutions, a PSMA specific inhibitor 2-(Phosphonomethyl)-pentandioic acid (2-PMPA) (final concentration 10 μM) was also added at the same time and incubated at 37° C. for 15 hours.
(3) Each solution after the incubation in (2) was diluted to 2800 μL with 200 mM Na-Pi buffer, and the fluorescence spectrum was measured.

FIG. 1 illustrates the fluorescence spectrum of 5-fluAF-Glu and 6-fluAFGlu after addition of PSMA and an inhibitor (2-PMPA, 10 μM) (S/N to 417 at 516 nm). Table 2 illustrates an apparent dynamic parameter of 6-fluAFGlu (Compound 25) containing PSMA.

TABLE 2

|  | $K_m$ | $k_{cat}$ [s$^{-1}$] | $k_{cat}/K_m$ [M$^{-1} \cdot$ s$^{-1}$] |
|---|---|---|---|
| 6-fluAFGlu | 2.4 | $5.5 \times 10^{-4}$ | $0.23 \times 10^3$ |

Similarly, when carboxypeptidase M (CPM) was applied to 6-fluAFLys (Compound 26) and carboxypeptidase A (CPA) was applied to 6-fluAFPhe (Compound 27), the fluorescence rise due to the enzymatic reaction was observed.

<CPM>

(1) First to third solutions prepared by dissolving 10 μM probe in 200 μL of assay buffer were provided.
(Assay buffer: 50 mM MES, 0.2% Triton X-100, 5 mM $CaCl_2$, pH 6.0)
(2) 0.83 μg of CPM was added to the first solution in (1), 0.83 μg of CPM and a CPM specific inhibitor 3-(2-guanidinoethylthio)-2-(mercaptometyl)propanoic acid (MGTA) with a final concentration of 10 μM was added to the second solution, and the third solution was incubated at 37° C. for 2.5 hours without adding CPM and the specific inhibitor of CPM.
(3) 200 μL of each solution after the incubation in (2) was diluted with 2800 μL of 200 mM Na-Pi buffer, and the fluorescence spectrum was measured.

FIG. 2 illustrates the fluorescence spectrum of 6-fluAFLys after addition of CPM and an inhibitor (MGTA, 10 μM) (S/N to 72 at 514 nm).

<CPA>

(1) First to third solutions prepared by dissolving 10 μM probe in 600 μL of each assay buffer were provided.
(Assay buffer: Tris-buffered saline (TBS)) (2) 2 μg of CPA was activated with 18 μL of 5 ng/mL trypsine solution for 1 hour
(3) 9 μL of the solution in (2) was added to the solution in (1), and the mixture was incubated at 37° C. for 5 hours. For one of the solutions, a CPA specific inhibitor; potato carboxypeptidase inhibitor (final concentration 10 μg/mL) was also added at the same time and incubated at 37° C. for 5 hours.
(4) 200 μL of each solution after the incubation in (3) was diluted to 2800 μL with 200 mM Na-Pi inhibitor, and the fluorescence spectrum was measured.

FIG. 3 illustrates the fluorescence spectrum of 6-fluAFPhe after addition of CPA1 and an inhibitor (potato carboxypeptidase inhibitor, 10 μM) (S/N to 13 at 517 nm). woCPA in the figure is the result when CPA1 is not added.

Example 3

Cell Lysate Assay

When cell lysates of LNCaP as a PSMA expressing prostate cancer cell and PC3 as PSMA non-expressing prostate cancer cell were prepared and 6-fluAFGlu (Compound 25) was added to each, a significant increase in fluorescence was observed in the LNCaP cell lysate, and on the other hand, almost no increase in fluorescence was observed in the PC3 cell lysate and the LNCaP cell lysate to which a PSMA specific inhibitor 2-PMPA was added.

(1) 6-fluAFGlu with a final concentration of 10 μM was added to each cell lysate whose protein concentration was adjusted to 0.2 mg/mL, and while incubating at 37° C., the fluorescence intensity was measured over time using a plate reader. A PSMA specific inhibitor 2-PMPA (10 μM) was added to one of LNCaP cell lysate samples at the same time, and measurement was performed.
(2) The obtained fluorescence intensity of each lysate was normalized based on 0 minutes being set to 1, and then plot was performed with the incubation time on the horizontal axis.

FIG. 4 illustrates relative fluorescence intensity of 6-fluAFGlu after addition of a cell lysate and an inhibitor (2-PMPA, 10 μM).

Example 4

Live Cell Assay

LNCaP as a PSMA expressing cell and PC3 as a PSMA non-expressing cell were cultured on a 96-well plate, a 10 μM aqueous solution of 6-fluAFGlu (Compound 25) was added thereto, and the cells were observed over time. As a result, a significant increase in fluorescence intensity was observed in LNCaP compared to PC3. The increase in fluorescence in LNCaP was significantly suppressed by a PSMA specific inhibitor 2-PMPA.

(1) LNCaP and PC3 were cultured on a 96-well plate coated with poly-L-lysine, and the experiment was performed once a cell density reached about 90% confluent.
(2) A solution in each well was replaced with a 10 μM 6-fluAFGlu TBS solution, and the fluorescence intensity of the well was measured over time using a plate reader.
(3) The obtained fluorescence intensity value of each well was normalized based on 0 minutes being set to 1, and then plot was performed with the incubation time on the horizontal axis.

FIG. 5 illustrates the relative fluorescence intensity of 6-fluAFGlu after addition of cultured cells and an inhibitor (2-PMPA, 10 μM). In the figure, * means $p<0.05$,  means $p<0.01$, and * means $p<0.001$.

Example 5

Study Using CPM Expressing Cultured Cells (MDCK Cells)
(1) Reactivity with Cell Lysate
200 μL of PBS solution of 6-fluAFLys (Compound 26) and MDCK cell lysate (0.2 mg/mL), which was a CPM expressing cultured cell, was reacted at 37° C., and a change in fluorescence intensity over time was measured. MGTA which was a CPM inhibitor was added to one sample.

Ex/em: 485/535 nm, n=3, 6-fluAFLys final concentration: 10 μM, inhibitor (MGTA) final concentration: 10 μM The results are illustrated in FIG. 6. While a significant increase in fluorescence was observed in the MDCK cell lysate, almost no increase in fluorescence was observed in the MDCK cell lysate to which MGTA was added.

(2) Live Cell Imaging
A 6-FDAAFLys (Compound 24) solution (final concentration: 10 μM) diluted with HBSS(+) was added to MDCK cells, and a fluorescence image was taken by a confocal microscope under the following conditions while culturing at 37° C. and 5% $CO_2$. The results are illustrated in FIG. 7 and FIG. 8.

Ex/em: 488/500-550 nm, Scale bar: 50 μm

Live cell imaging was performed using MDCK cells that highly express CPM, and an increase in fluorescence intensity in the cells was observed over time by adding 6-FDAAFLys. On the other hand, in the case of MDCK cells to which MGTA of a CPM inhibitor was added, the increase in fluorescence intensity was suppressed.

Synthesis Example 2

2Me5GluAF-TG (Compound 32), which was the fluorescent probe for detecting carboxypeptidase activity of the present invention, was synthesized by the following scheme 2.

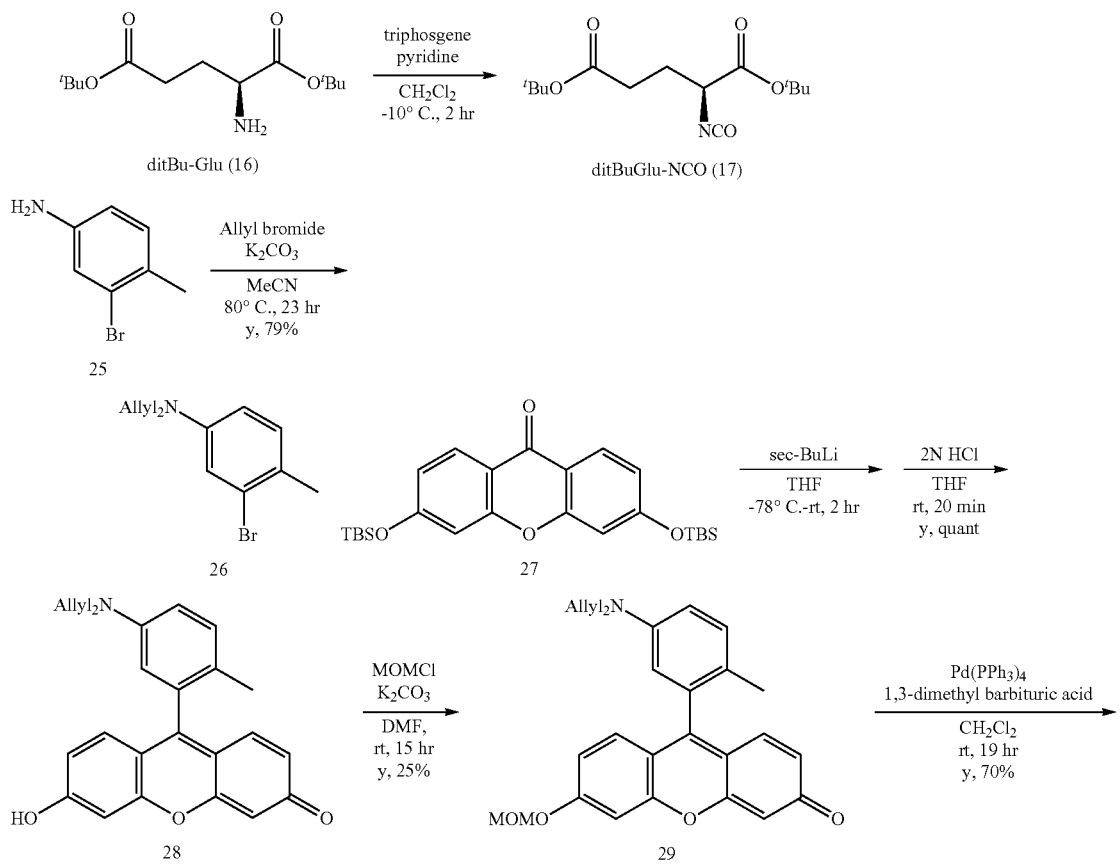

Scheme 2: Synthesis of fluorescent probe for detecting carboxypeptidase activity (2Me5GluAF-TG) (2)

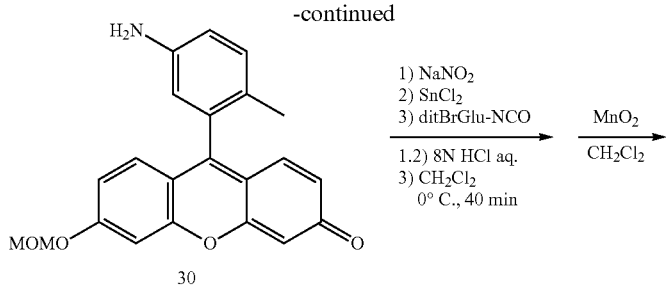

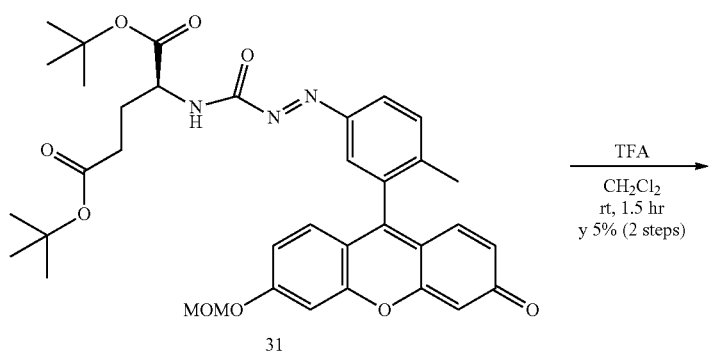

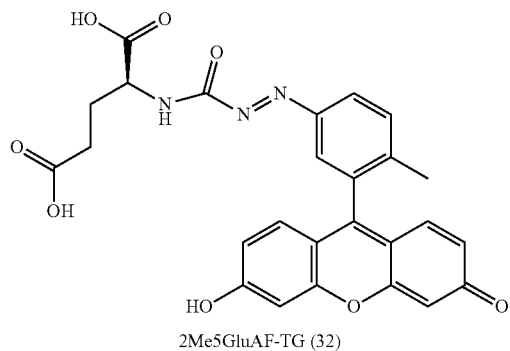

2Me5GluAF-TG (32)

(1) Synthesis of
N,N-diallyl-3-bromo-4-methylaniline (26)

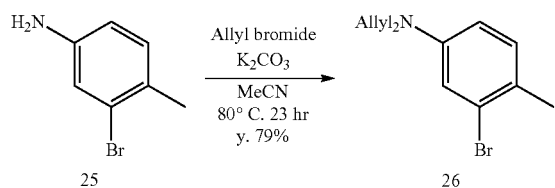

3-Bromo-4-methylaniline (25) (3.04 g, 0.016 mol, 1 eq) and potassium carbonate (3.38 g, 0.024 mol, 1.5 eq) were dissolved in 15 mL of acetonitrile, and allyl bromide (5.65 mL, 0.065 mol, 4 eq) was added. The mixture was stirred under an argon atmosphere at 80° C. for 23 hours. The solvent was distilled off under reduced pressure, and a residue was dissolved in dichloromethane and washed with water and saturated saline. After an organic layer was dried over anhydrous sodium sulfate, the solvent was distilled off under reduced pressure. A crude purified product was purified by silica gel column chromatography (solvent: hexane/ethyl acetate=100/0-85/15) to obtain Compound 26 (3.41 g, 79%).

$^1$H NMR (400 MHz, CDCl$_3$): δ. 7.07 (d, 1H, J=8.4 Hz), 6.94 (m, 1H), 6.61 (m, 1H), 5.91-5.84 (m, 2H), 5.24-5.20 (m, 4H), 3.92 (m, 4H), 2.33 (m, 4H); $^{13}$C NMR (100 MHz, CDCl$_3$): δ. 148.0, 133.6, 130.9, 125.6, 124.9, 116.3, 116.0, 111.7, 52.9, 21.6.

(2) Synthesis of 2Me5Allyl$_2$N-TG (28)

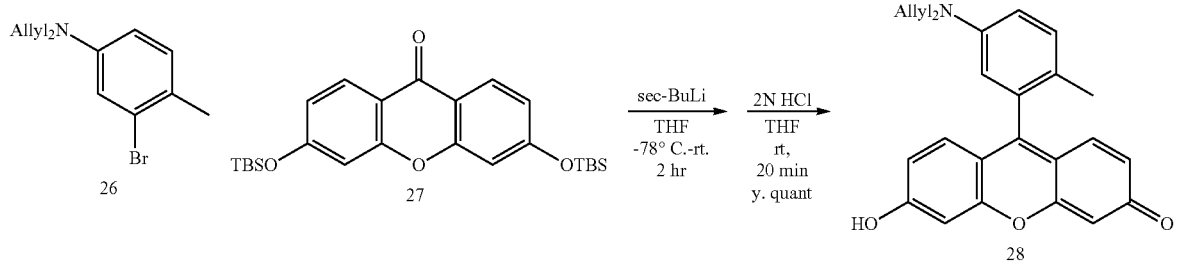

N,N-diallyl-3-bromo-4-methylaniline (26) (1.06 g, 3.99 mmol, 1 eq) was dissolved in 8 mL of tetrahydrofuran and stirred under an argon atmosphere at −78° C. for 10 minutes, and a 1M sec-butyl lithium cyclohexane/normal hexane solution (4 mL, 4 mmol, 1 eq) was slowly added dropwise. 15 minutes later, diTBS-xanthene (27) (synthesized according to Shieh, P., Hangauer, M. J. & Bertozzi, C. R. Fluorogenic Azidofluoresceins for Biological Imaging. J. Am. Chem. Soc. 134, 17428-17431 (2012)) (1.82 g, 3.99 mmol, 1 eq) dissolved in 11 mL of tetrahydrofuran was added, and the mixture was stirred under an argon atmosphere for 1 hour while returning to room temperature. 2 mL of 2N hydrochloric acid was added, the mixture was stirred at room temperature for 20 minutes, and then Compound 28 (1.58 g) was obtained as a crude product by filtration.

HRMS-ESI (m/z): [M+H]$^+$ calcd for 398.17507 ($C_{26}H_{24}NO_3$), found 398.17548 (−0.4 mmu).

(3) Synthesis of 2Me5Allyl$_2$N-TG-MOM(29)

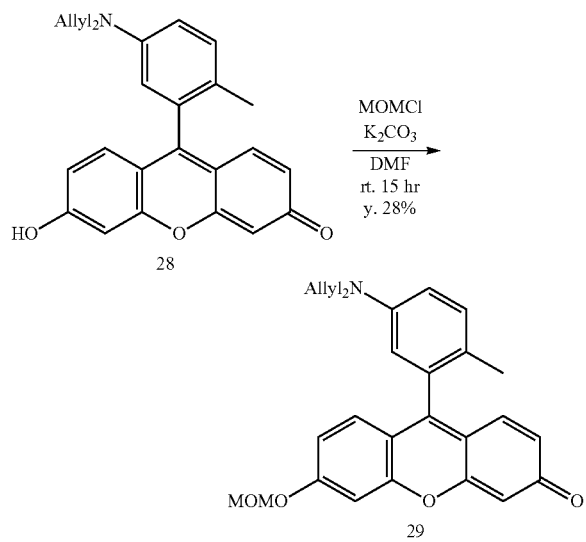

2Me5Allyl$_2$N-TG (28) (500.8 mg, 1.26 mmol, 1 eq) and potassium carbonate (209.6 mg, 1.52 mmol, 1.2 eq) were dissolved in 10 mL of N,N-dimethylformamide, and chloromethyl methyl ether (143 μL, 1.88 mmol, 1.5 eq) was added. The mixture was stirred at room temperature for 15 hours. The solvent was distilled off under reduced pressure, and a residue was dissolved in dichloromethane and washed with water and saturated saline. After an organic layer was dried over anhydrous sodium sulfate, the solvent was distilled off under reduced pressure, and crude purification was performed by silica gel column chromatography (solvent: hexane/ethyl acetate=80/20-50/50), and 2Me5Allyl$_2$N-TG-MOM (29) (153.3 mg) was obtained as a crude product.

(4) Synthesis of 2Me5NH$_2$-TG-MOM (30)

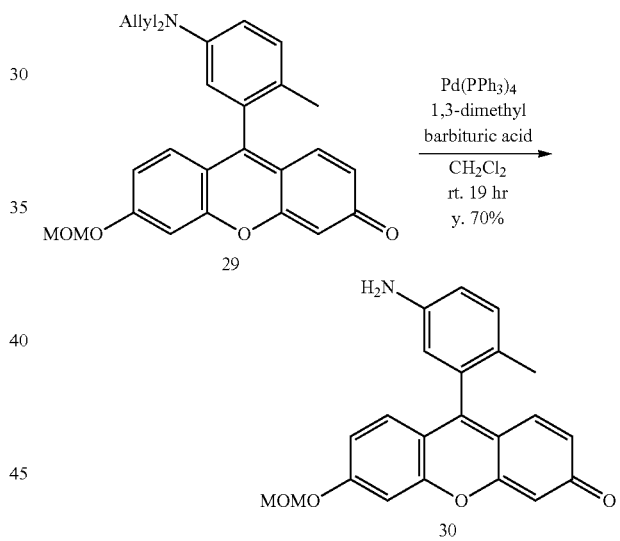

2Me5Allyl$_2$N-TG-MOM (29) (269.7 mg, 0.61 mmol, 1 eq), 1,3-dimethylbarbituric acid (764.3 mg, 4.89 mmol, 8 eq), and tetrakis(triphenylphosphine)palladium (0) (143.4 mg, 0.12 mmol, 0.2 eq) were dissolved in 10 mL of deoxygenated dichloromethane and the mixture was stirred at room temperature for 19 hours. The solvent was distilled off under reduced pressure, and a residue was roughly purified by silica gel column chromatography (solvent: dichloromethane/methanol=100/0-90/10). In addition, purification was performed by preparative TLC (solvent: hexane/ethyl acetate=2/1) to obtain 2Me5NH$_2$-TG-MOM (30) (154.8 mg, 70%).

$^1$H NMR (400 MHz, CD$_3$OD): δ. 7.31 (d, 1H, J=2.4 Hz), 7.25 (d, 1H, J=9.0 Hz), 7.21 (d, 1H, J=9.6 Hz), 7.18 (d, 1H, J=8.3 Hz), 7.06 (dd, 1H, J=9.0 Hz, 2.4 Hz), 6.87 (dd, 1H, J=8.3 Hz, 2.4 Hz), 6.62 (dd, 1H, J=9.6 Hz, 2.0 Hz), 6.59 (d, 1H, J=2.4 Hz), 6.49 (d, 1H, J=2.0 Hz), 5.37 (s, 2H), 3.50 (s, 3H), 1.9 (s, 3H); $^{13}$C NMR (101 MHz, CD$_3$OD): δ. 187.5, 164.5, 161.6, 156.3, 155.8, 147.3, 133.8, 133.2, 132.4, 131.5, 129.6, 125.6, 118.8, 118.0, 116.6, 116.5, 116.3, 105.6, 104.0, 95.8, 56.9, 18.5. HRMS-ESI (m/z): [M+H]$^+$ calcd for 362.13868 ($C_{22}H_{20}NO_4$), found 362.13958 (−0.9 mmu).

(5) Synthesis of 2Me5GluAF-TG (Compound 32)

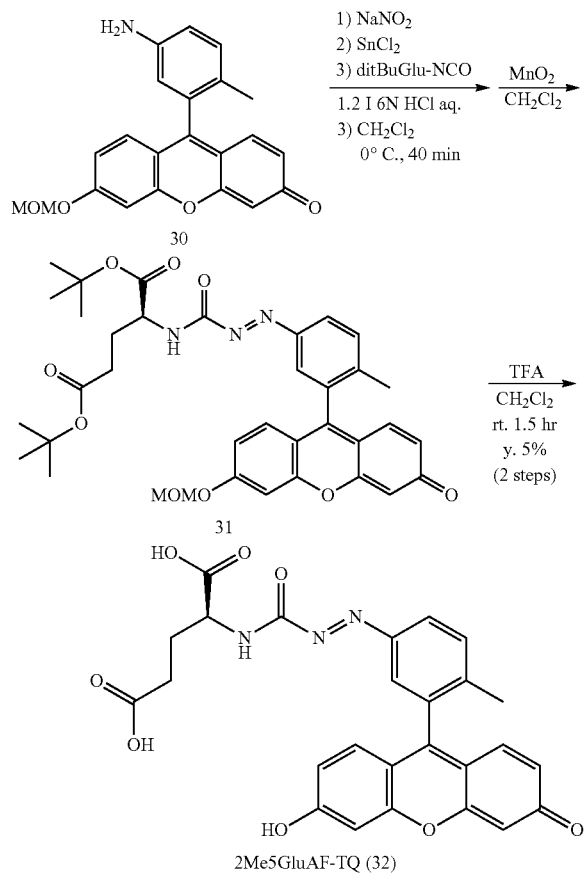

2Me5NH$_2$-TG-MOM (30) (29.5 mg, 0.082 mmol, 1 eq) was dissolved in 0.5 mL of 6N hydrochloric acid previously cooled to 4° C., and a reaction solution was cooled to 0° C. Sodium nitrite (5.07 mg, 0.073 mmol, 0.9 eq) dissolved in 0.1 mL of water was added dropwise and stirred at 0° C. for 5 minutes. Tin (II) chloride (13.93 mg, 0.073 mmol, 0.9 eq) dissolved in 0.1 mL of 1N hydrochloric acid was added dropwise, and immediately after that, ditBuGlu-NCO (58 mg, 0.20 mmol, 2.4 eq) dissolved in 1 mL of dichloromethane was added. Then, a 2N aqueous sodium hydroxide solution was added until the pH reached 11 or more, and the mixture was vigorously stirred at 0° C. for 40 minutes. 2N hydrochloric acid was added until the pH reached 7, and the mixture was extracted three times with dichloromethane. An organic layer was washed with saturated saline and dried over anhydrous sodium sulfate, and the anhydrous sodium sulfate was removed by filtration. An excess amount of manganese dioxide was added to the filtrate, and the mixture was stirred at room temperature for 20 minutes. Manganese dioxide was removed by Celite filtration, and the solvent was distilled off under reduced pressure. A residue was purified by semi-preparative HPLC to give an intermediate. 0.5 mL of dichloromethane and 0.5 mL of trifluoroacetic acid were added to a compound, and the mixture was stirred at room temperature for 1 hour. The solvent was distilled off under reduced pressure, and a residue was purified by semi-preparative HPLC to give 2Me5GluAF-TG (Compound 32) (1.9 mg, 4.6% (2 steps)).

$^1$H NMR (400 MHz, CD$_3$OD): δ. 8.20 (dd, 1H, J=8.3 Hz, 2.0 Hz), 7.94 (d, 1H, J=2.0 Hz), 7.79 (d, 1H, J=8.3 Hz), 7.49 (d, 1H, J=9.3 Hz), 7.23 (d, 1H, J=2.2 Hz), 7.12 (dd, 1H, J=9.3 Hz, 2.2 Hz), 4.60-4.56 (m, 1H), 2.51-2.47 (m, 2H), 2.38-2.29 (m, 1H), 2.17 (s, 3H), 2.13-2.03 (m, 1H); $^{13}$C NMR (101 MHz, CD$_3$OD): δ. 176.2, 174.4, 174.0, 163.8, 160.8, 150.9, 143.9, 134.2, 133.6, 133.5, 126.4, 125.6, 122.3, 117.6, 104.0, 54.4, 31.1, 27.8, 20.0. One of the peaks of the quaternary carbon is missing HRMS-ESI (m/z): [M+H]$^+$ calcd for 504.14014 ($C_{26}H_{22}N_3O_8$), found 504.13930 (+0.8 mmu).

Example 5

Absorption/Fluorescence Spectrum Measurement of 2Me5GluAF-TG (Compound 32)

FIG. 9 and FIG. 10 illustrate the results of the absorption/fluorescence spectrum measurement of 2Me5GluAF-TG (Compound 32). It was revealed that 2Me5GluAF-TG (Compound 32) had almost no fluorescencence under physiological conditions as compared to highly fluorescent fluorescein. The absorption spectrum was measured using UV-2450 (SIMADZU), and the fluorescence spectrum was measured using F-7000 (HITACHI).

Table 3 describes the spectroscopic properties of 2Me5GluAF-TG (Compound 32).

TABLE 3

| | $\lambda_{abs}$ (nm) | $\lambda_{em}$ (nm) | $\Phi_{fl}$* |
|---|---|---|---|
| 2Me5GluAF-TG | 495 | 516 | 0.002 |

*measured with 0.2M phosphate buffer (pH 7.4)

Example 6

Enzyme Assay (1) Reactivity with PSMA Purified Enzyme

A solution (10 μM, 200 μL) of 2Me5GluAF-TG (Compound 32) and recombinant human PSMA (0.44 μg) were reacted in 1×TBS buffer at 37° C., and the fluorescence intensity was measured every 30 minutes. Inhibitor (2-PMPA) concentration: 10 μM, Ex/em: 485/535 nm·n=3.

The change in fluorescence intensity due to the enzyme reaction was measured in the same manner as in the method described in Example 2. The results are illustrated in FIG. 11.

When PSMA was applied to 2Me5GluAF-TG (Compound 32), the increase in fluorescence due to the enzymatic reaction was observed. No increase in fluorescence was observed in the presence of the inhibitor (2-PMPA).

FIG. 12 illustrates a plotted fluorescence increase rate in an initial stage of the reaction when PSMA is added to 2Me5GluAF-TG (Compound 32) solutions of various concentrations, and Table 4 illustrates the apparent dynamic parameter of 2Me5GluAF-TG and 6-fluAFGlu (Compound 25).

TABLE 4

|  | $K_m$ (μM) | $k_{cat}$ (s$^{-1}$) | $k_{cat}/K_m$ (M$^{-1}$·s$^{-1}$) |
|---|---|---|---|
| 6GluAF-Flu | 5.0 | 0.001 | 200 |
| 2Me5GluAF-TG | 4.3 | 0.066 | 15344 |

(2) LC-UV/MS Analysis of Reaction Solution

A solution, prepared after recombinant human PSMA and 2Me5GluAF-TG (Compound 32) were reacted for 10 hours, and 2Me5GluAF-TG and 2MeTG synthesized as preparations were subjected to LC-UV/MS analysis.

Probe concentration: 10 μM (2Me5GluAF-TG, enzyme reaction solution), 2 μM (2MeTG). The results are illustrated in FIG. 13 and FIG. 14.

From the above results, it was confirmed that 2MeTG and 2Me5OH-TG exhibiting fluorescence in the presence of PSMA were produced. It was shown that 2Me5GluAF-TG was stable when an inhibitor (2-PMPA) was added or in the absence of PSMA.

Example 7

Study Using Cultured Cells Derived from Prostate Cancer
(1) Reactivity with Cell Lysate A solution (20 μM, 100 μL) of 2Me5GluAF-TG (Compound 32) and a cell lysate (0.36 mg/mL, 100 μL) were reacted in TBS-T buffer at 37° C., and the fluorescence intensity was measured every 30 minutes. The measurement procedure is as described in Example 3.

Ex/em: 485/535 nm, n=3, probe final concentration: 10 μM, inhibitor (2-PMPA) concentration: 10 μM The results are illustrated in FIG. 15. While a significant increase in fluorescence was observed in LNCaP cell lysate, almost no increase in fluorescence was observed in PC3 cell lysate or LNCaP cell lysate to which a PSMA specific inhibitor 2-PMPA was added.
(2) Live Cell Imaging A solution (final concentration: 10 μM) of 2Me5GluAF-TG (Compound 32) diluted with HBSS(+) was added to LNCaP cells (high PSMA expression) or PC3 cells (PSMA non-expression), and a fluorescence image was taken by a confocal microscope every 1 hour under the following conditions while culturing at 37° C. and 5% $CO_2$.

Ex/em: 490/500-600 nm, Scale bar: 50 μm

The results are illustrated in FIG. 16 and FIG. 17. When LNCaP cells that highly express PSMA were used, the fluorescence intensity of the fluorescence image increased with the passage of time (FIG. 16). On the other hand, when PC3 cells that did not express PSMA were used, no change was observed in the fluorescence image (FIG. 17).
(3) Experiment for Inhibitor A probe (2Me5GluAF-TG) and an inhibitor were added, and after culturing at 37° C. and 5% $CO_2$ for 15 hours, a fluorescence image was taken with a confocal microscope. Probe concentration: 10 μM, inhibitor (2-PMPA) concentration: 10 μM, Ex/em: 490/500-600 nm, Scale bar: 50 μm.

Ten intracellular regions and ten extracellular regions were each surrounded by ROI, and an average value of the fluorescence intensity was calculated. FIG. 18*a* illustrates the taken fluorescence image, and FIG. 18*b* illustrates the average value of the fluorescence intensity with and without addition of the inhibitor.

FIG. 18*a* illustrates that when the inhibitor is added, the intensity of the fluorescence image does not increase. The graph on the left side of FIG. 18*b* (when no inhibitor is added) illustrates that the average value of the fluorescence intensity inside the cell is much higher than that outside the cell. This suggests that 2Me5GluAF-TG is a fluorescent probe that is more easily taken up into cells.
(4) LC-UV/MS Analysis of Extracellular Fluid After imaging of LNCaP cells using 2Me5GluAF-TG, a collected extracellular fluid, and 2Me5GluAF-TG and 2MeTG synthesized as preparations were subjected to the LC-MS analysis under the following conditions.

Probe concentration: 10 μM (2Me5GluAF-TG, extracellular fluid), 2 μM (2MeTG).

The results are illustrated in FIG. 19 and FIG. 20.

From the above results, production of fluorescent 2MeTG was confirmed in the absence of the inhibitor (2-PMPA). 2MeTG was not produced when the inhibitor was added, indicating that 2Me5GluAF-TG was stable.

Example 8

Study Using Human Prostate Cancer Surgical Specimen

Using 2Me5GluAF-TG, a study was conducted using a human prostate cancer surgical specimen according to the following protocol.
<Protocol>
1. Wash surgical specimen with 1×TBS buffer
2. Add dropwise 2.50 μM of 2Me5GluAF-TG solution (diluted with 1×TBS buffer) so that the whole specimen is immersed.
3. While heating to 40° C. with a heater, take a fluorescence image by Maestro for up to 4 hours
4. Judge from the fluorescence image taken 4 hours after immersion, select and cut out several sites showing bright fluorescence and several sites showing no fluorescence, and fix with a 10% formalin solution
5. Request a pathologist to perform HE staining/PSMA immunostaining on each site and evaluate a rate of cancer sites and PSMA expression The results of using four types of specimens are illustrated in FIG. 21 to FIG. 24. FIG. 25 illustrates a result obtained by changing the above protocol (changing a method so that a surface is covered with gauze soaked in a probe solution, temporarily removing the gauze, and taking a fluorescence image).
 (a) of each figure illustrates a photograph before immersion of the surgical specimen in a Me5GluAF-TG solution and a photograph taken 4 hours after the immersion (the right side is a fluorescence image). The graph on the left side of (b) illustrates a change in fluorescence intensity at a selected site of the surgical specimen from the immersion in the Me5GluAF-TG solution to 4 hours after the immersion. (c) illustrates results of evaluation of the PSMA expression, rate of cancer sites, and GS at each site. Here, GS is an index for evaluating a malignant tumor, and the higher the value, the higher cancer aggressiveness.

FIG. 26 summarizes the increase rate of the fluorescence intensity after 30 minutes, 60 minutes, and 240 minutes of each site subjected to specimen imaging. Here, the black bar graph indicates the site including the cancer site, and the white bar graph indicates the site not including the cancer site.

These results suggest that there is a rough correlation between the increase in fluorescence intensity and the presence or absence of the cancer site or a PSMA expression level and 2Me5GluAF-TG may be used as a prostate cancer imaging probe.

What is claimed is:

1. A compound represented by the following general formula (I) or a salt thereof:

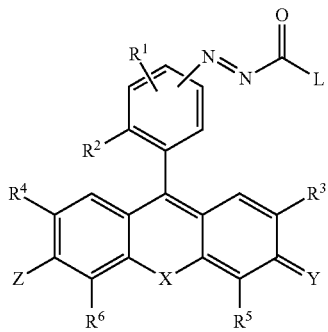

wherein
- $R^1$ represents a hydrogen atom or one to three monovalent substituent groups present on a benzene ring, which are the same or different;
- $R^2$ represents a monovalent substituent group present on a benzene ring;
- $R^3$ and $R^4$ are, each independently, a hydrogen atom, an alkyl group having 1 to 6 carbon atoms, or a halogen atom;
- $R^5$ and $R^6$ are, each independently, a hydrogen atom, an alkyl group having 1 to 6 carbon atoms, or a halogen atom;
- L represents an amino acid residue;
- X is selected from an oxygen atom, $Si(R^a)(R^b)$, $C(R^a)(R^b)$, $Ge(R^a)(R^b)$, $P(=O)R^c$ or Se
where:
- $R^a$ and $R^b$ are, each independently, an alkyl group having 1 to 6 carbon atoms or an aryl group optionally being substituted, and $R^c$ is an alkyl group having 1 to 6 carbon atoms or a phenyl group optionally being substituted;
- Y and Z are selected from a pair of (O, OH), ($NR^7R^8$, $NR^9R^{10}$), and (O, $NR^9R^{10}$) where:
  - $R^7$ and $R^8$ are, each independently, a hydrogen atom or an alkyl group having 1 to 3 carbon atoms;
  - $R^7$ and $R^8$ together optionally form a 4-7 membered heterocyclyl containing a nitrogen atom to which $R^7$ and $R^8$ are bonded;
  - $R^7$ or $R^8$, or both $R^7$ and $R^8$, together with $R^3$ and/or $R^5$, respectively, optionally form a 5-7 membered heterocyclyl or heteroaryl containing a nitrogen atom to which $R^7$ and/or $R^8$ are bonded, and optionally contain from one to three heteroatoms selected from the group consisting of an oxygen atom, nitrogen atom, and sulfur atom as ring-constituting members, and the heterocyclyl or heteroaryl is optionally substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms;
  - $R^9$ and $R^{10}$ are, each independently, a hydrogen atom or an alkyl group having 1 to 3 carbon atoms;
  - $R^9$ and $R^{10}$ together optionally form a 4-7 membered heterocyclyl containing a nitrogen atom to which $R^9$ and $R^{10}$ are bonded;
  - $R^9$ or $R^{10}$, or both $R^9$ and $R^{10}$, together with $R^4$ and/or $R^6$, respectively, optionally form a 5-7 membered heterocyclyl or heteroaryl containing a nitrogen atom to which $R^9$ and/or $R^{10}$ are bonded, and optionally contain from one to three heteroatoms selected from the group consisting of an oxygen atom, nitrogen atom, and sulfur atom as ring-constituting members, and the heterocyclyl or heteroaryl is optionally substituted by alkyl having 1 to 6 carbon atoms, alkenyl having 2 to 6 carbon atoms, alkynyl having 2 to 6 carbon atoms, aralkyl group having 6 to 10 carbon atoms, or alkyl-substituted alkenyl group having 6 to 10 carbon atoms; and
- when Y and Z are O and OH, respectively, and when a monovalent substituent group present on a benzene ring of $R^2$ is a carboxyl group, Y and Z are optionally acetylated.

2. The compound or salt thereof according to claim 1, wherein L is represented by the following formula:

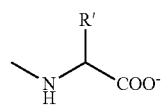

wherein R' represents a side chain of an amino acid.

3. The compound or salt thereof according to claim 1, wherein the monovalent substituent of $R^2$ is selected from an alkyl group having 1 to 6 carbon atoms, a hydroxyalkyl group having 1 to 6 carbon atoms, an alkoxy group having 1 to 6 carbon atoms, an aminoalkyl group having 1 to 6 carbon atoms, a carboxyl group, an alkoxycarbonyl group, an amide group or a carboxamide group optionally having a substituent on nitrogen.

4. The compound or salt thereof according to claim 1, wherein X is an oxygen atom.

5. A compound represented by the following general formula (V) or salt thereof:

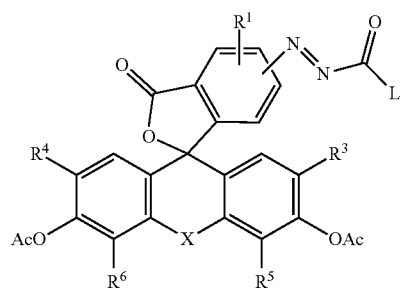

wherein
- $R^1$ represents a hydrogen atom or one to three monovalent substituent groups present on a benzene ring, which are the same or different;
- $R^3$ and $R^4$ are, each independently, a hydrogen atom, an alkyl group having 1 to 6 carbon atoms, or a halogen atom;
- $R^5$ and $R^6$ are, each independently, a hydrogen atom, an alkyl group having 1 to 6 carbon atoms, or a halogen atom;
- L represents an amino acid residue;
- X is selected from an oxygen atom, $Si(R^a)(R^b)$, $C(R^a)(R^b)$, $Ge(R^a)(R^b)$, $P(=O)R^c$ or Se where:
R$^a$ and R$^b$ are, each independently, an alkyl group having 1 to 6 carbon atoms or an aryl group optionally being substituted, and R$^c$ is an alkyl group having 1 to 6 carbon atoms or a phenyl group optionally being substituted;
wherein Ac represents an acetyl group.

6. A compound selected from the group consisting of the following formulas, or a salt thereof:

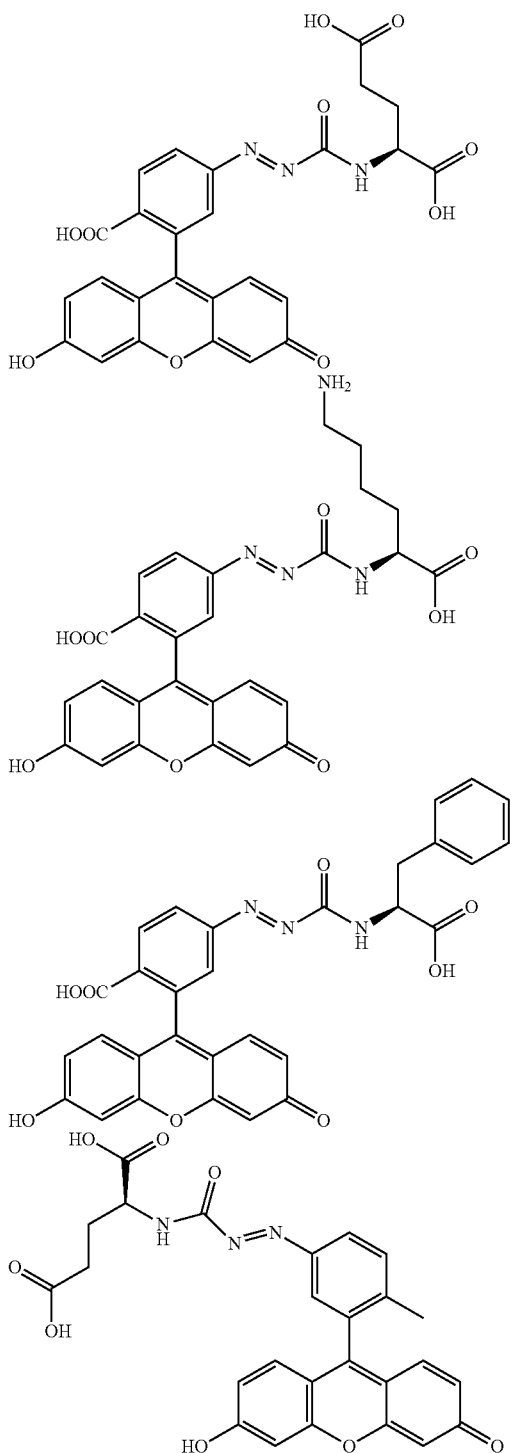

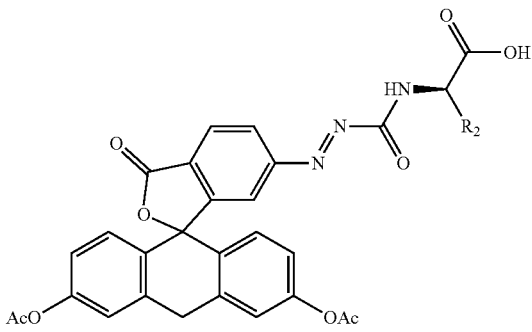

wherein R$_2$ is $CH_2CH_2COOH$ or $CH_2CH_2CH_2CH_2NH_2$.

7. A fluorescent probe for detecting carboxypeptidase activity comprising the compound or salt thereof according to claim 1.

8. A method of detecting carboxypeptidase in a cell, comprising:
(a) introducing the fluorescent probe according to claim 7 into the cell; and
(b) measuring fluorescence emitted in the cell by the fluorescent probe.

9. A method of detecting a prostate cancer, comprising:
(a) applying the fluorescent probe according to claim 7 to a clinical specimen of prostate; and
(b) measuring a fluorescence image of the clinical specimen of the prostate to which the fluorescent probe is applied.

10. The method of claim 9, wherein the clinical specimen of prostate is a surgical specimen.

11. A fluorescent probe for detecting carboxypeptidase activity comprising the compound or salt thereof according to claim 5.

12. A method of detecting carboxypeptidase in a cell, comprising:
(a) introducing the fluorescent probe according to claim 11 into the cell; and
(b) measuring fluorescence emitted in the cell by the fluorescent probe.

13. A method of detecting a prostate cancer, comprising:
(a) applying the fluorescent probe according to claim 11 to a clinical specimen of prostate; and
(b) measuring a fluorescence image of the clinical specimen of the prostate to which the fluorescent probe is applied.

14. The method of claim 13, wherein the clinical specimen of prostate is a surgical specimen.

* * * * *

UNITED STATES PATENT AND TRADEMARK OFFICE
CERTIFICATE OF CORRECTION

PATENT NO. : 12,055,546 B2
APPLICATION NO. : 16/977434
DATED : August 6, 2024
INVENTOR(S) : Yasuteru Urano It is certified that error appears in the above-identified patent and that said Letters Patent is hereby corrected as shown below:

In the Specification

In Column 4, Line 15, delete "0" and insert --O--.

In Column 4, Line 44 (Approx.), delete "0" and insert --O--.

In Column 6, Line 54, delete "PM)." and insert --µM).--.

In Column 9, Line 62, delete "$R^C$" and insert --$R^c$--.

In Column 11, Line 22, delete "0" and insert --O--.

In Column 27, TABLE 2, Line 49 (Approx.), delete "$K_m$" and insert --$K_m$ [mM]--.

Signed and Sealed this
Eighteenth Day of March, 2025

Coke Morgan Stewart
*Acting Director of the United States Patent and Trademark Office*